United States Patent [19]
Zehner et al.

[11] Patent Number: 5,605,735
[45] Date of Patent: Feb. 25, 1997

[54] HIGH-PEEL TAB FASTENER

[75] Inventors: Georgia L. Zehner, Larsen; Paul T. VanGompel, Hortonville; Thomas H. Roessler, Menasha; Yung H. Huang, Appleton, all of Wis.

[73] Assignee: Kimberly-Clark Corporation, Neenah, Wis.

[21] Appl. No.: 366,080

[22] Filed: Dec. 28, 1994

[51] Int. Cl.⁶ .............................. A61F 13/56; B32B 3/06
[52] U.S. Cl. .................... 428/100; 428/192; 428/194; 428/343; 428/354; 604/389; 604/390; 604/391
[58] Field of Search .................... 428/40, 100, 343, 428/354, 192, 194; 604/389, 390, 391

[56] References Cited

U.S. PATENT DOCUMENTS

| | | | |
|---|---|---|---|
| 3,901,236 | 8/1975 | Assarsson et al. | 128/284 |
| 3,920,016 | 11/1975 | Mesek et al. | 128/287 |
| 4,005,713 | 2/1977 | Mesek | 128/287 |
| 4,049,001 | 9/1977 | Tritsch | 128/287 |
| 4,074,716 | 2/1978 | Schaar | 128/287 |
| 4,076,663 | 2/1978 | Masuda et al. | 260/17.4 |
| 4,158,363 | 6/1979 | Schaar | 128/287 |
| 4,227,530 | 10/1980 | Schatz | 128/287 |
| 4,286,082 | 8/1981 | Tsubakimoto et al. | 526/240 |
| 4,663,220 | 5/1987 | Wisneski et al. | 428/221 |
| 4,670,012 | 6/1987 | Johnson | 604/390 |
| 4,699,823 | 10/1987 | Kellenberger et al. | 428/219 |
| 4,704,116 | 11/1987 | Enloe | 604/385 |
| 4,753,646 | 6/1988 | Enloe | 604/385 |
| 4,753,649 | 6/1988 | Pazdernik | 604/389 |
| 4,778,701 | 10/1988 | Pape | 428/40 |
| 4,834,820 | 5/1989 | Kondo et al. | 156/73.3 |
| 4,869,724 | 9/1989 | Scripps | 604/389 |
| 4,916,005 | 4/1990 | Lippert et al. | 428/192 |
| 4,938,753 | 7/1990 | Van Gompel et al. | 604/385.2 |
| 5,019,073 | 5/1991 | Roessler et al. | 604/391 |
| 5,024,672 | 6/1991 | Widlund | 604/390 |
| 5,147,347 | 9/1992 | Huang et al. | 604/390 |
| 5,192,606 | 3/1993 | Proxmire et al. | 428/284 |
| 5,226,992 | 7/1993 | Morman | 156/62.4 |
| 5,288,546 | 2/1994 | Roessler et al. | 428/284 |
| 5,399,219 | 3/1995 | Roessler | 156/259 |

FOREIGN PATENT DOCUMENTS

| | | |
|---|---|---|
| 0217032A3 | 4/1987 | European Pat. Off. |
| 0338680 | 10/1989 | European Pat. Off. |
| 0233704B1 | 7/1992 | European Pat. Off. |
| 2091986 | 8/1982 | United Kingdom. |
| 2238462 | 6/1991 | United Kingdom. |
| 9007313 | 7/1990 | WIPO. |

*Primary Examiner*—Nasser Ahmad
*Attorney, Agent, or Firm*—Paul Yee

[57] ABSTRACT

A distinctive fastening tab includes a fastener substrate having a construction-bond portion, a user-bond portion, a user-bond end section, a construction-bond end section, a pair of opposed side edge sections, a fastening surface and a user surface. A securing means connects to the fastening surface of the fastener substrate at least along the user-bond portion thereof, and a gripping member connects to the user surface at the user-bond portion of the fastener substrate. The gripping member has a distal end portion which is substantially free, and a base portion which is operably connected to the user surface of the fastener substrate. The gripping member is configured to intersect the fastener substrate at a location which is spaced from the construction-bond portion and is positioned between the construction-bond portion and the user-bond end section of the fastener substrate.

33 Claims, 17 Drawing Sheets

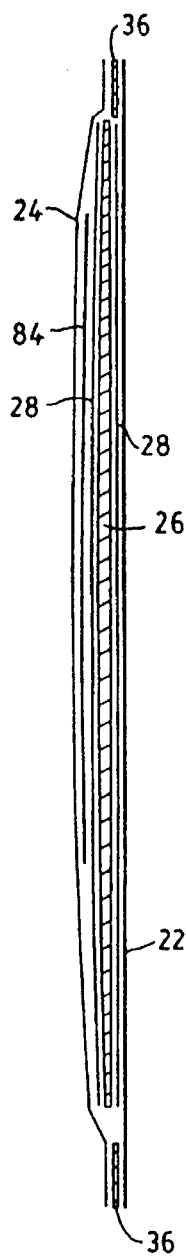
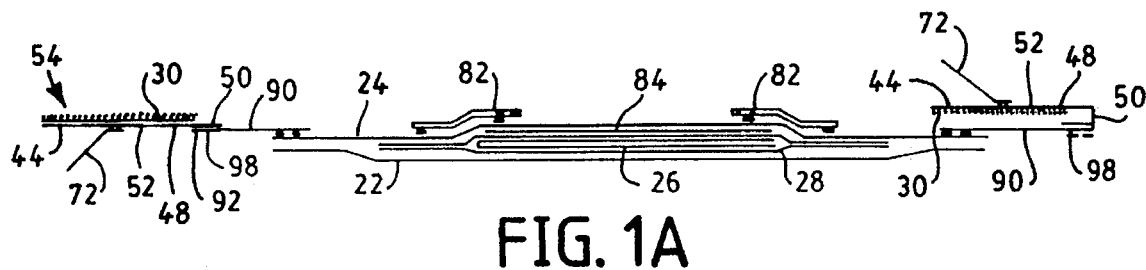
FIG. 1B
FIG. 1A

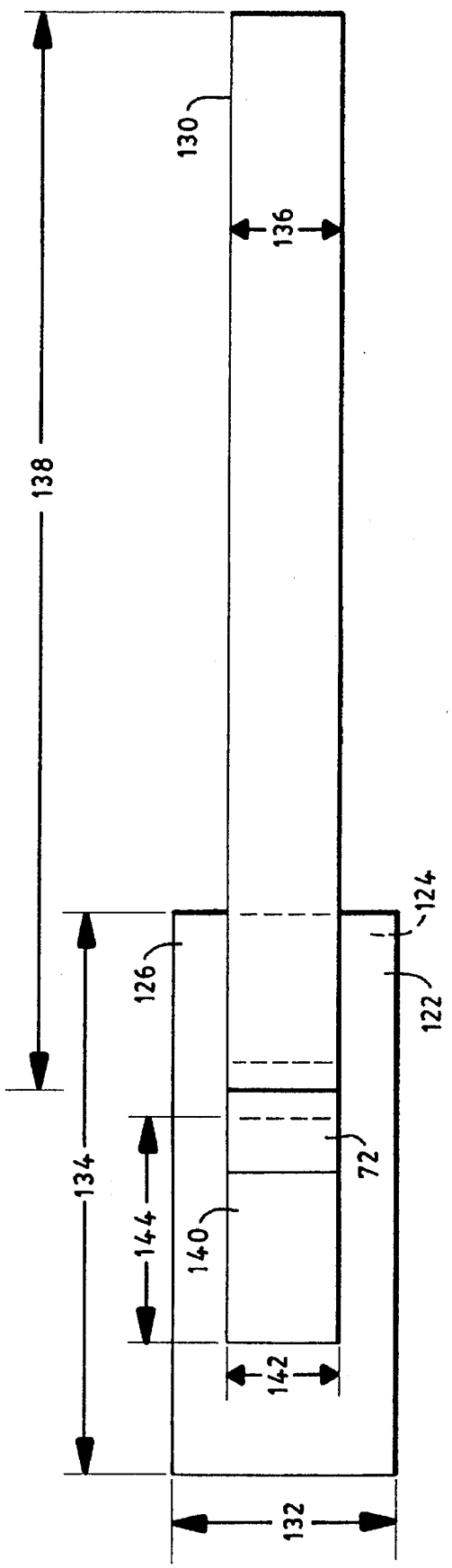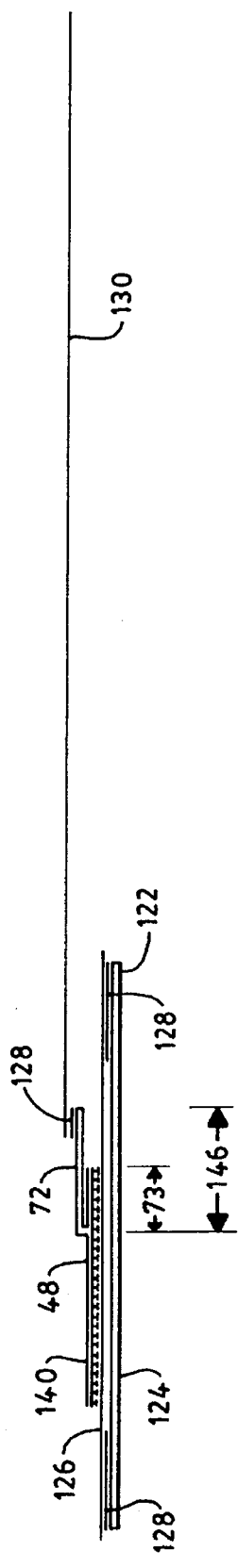
FIG. 7
FIG. 7A

EFFECTS OF TAB OFFSET LOCATION
PEAK FORCE (GRAMS/CM)

| SAMPLE NO. | CODE A | CODE B | CODE C | CODE D |
|---|---|---|---|---|
| 1 | 20 | 87 | 159 | 228 |
| 2 | 17 | 91 | 165 | 421 |
| 3 | 10 | 57 | 122 | 366 |
| 4 | 12 | 87 | 102 | 362 |
| 5 | 14 | 98 | 118 | 551 |
| AVG | 14 | 84 | 133 | 386 |

FIG. 11

EFFECTS OF TAB OFFSET LOCATION
PEAK FORCE (GRAMS/CM)

| SAMPLE NO. | CODE C | CODE E | CODE F | CODE G |
|---|---|---|---|---|
| 1 | 159 | 291 | 307 | 307 |
| 2 | 165 | 252 | 260 | 309 |
| 3 | 122 | 280 | 398 | 264 |
| 4 | 102 | 335 | 272 | 205 |
| 5 | 118 | 169 | 386 | 201 |
| AVG | 133 | 265 | 324 | 257 |

FIG. 12

EFFECTS OF ATTACHMENT RIGIDITY
PEAK FORCE (GRAMS/CM)

| SAMPLE NO. | CODE C | CODE J | CODE H |
|---|---|---|---|
| 1 | 159 | 126 | 252 |
| 2 | 165 | 256 | 281 |
| 3 | 122 | 254 | * >181 |
| 4 | 102 | 205 | 264 |
| 5 | 118 | 193 | * >181 |
| AVG | 133 | 207 | ** 266 |

\* DELAMINATION FAILURE
\*\* AVERAGE IS OF SAMPLES 1, 2, AND 4 ONLY

FIG. 14

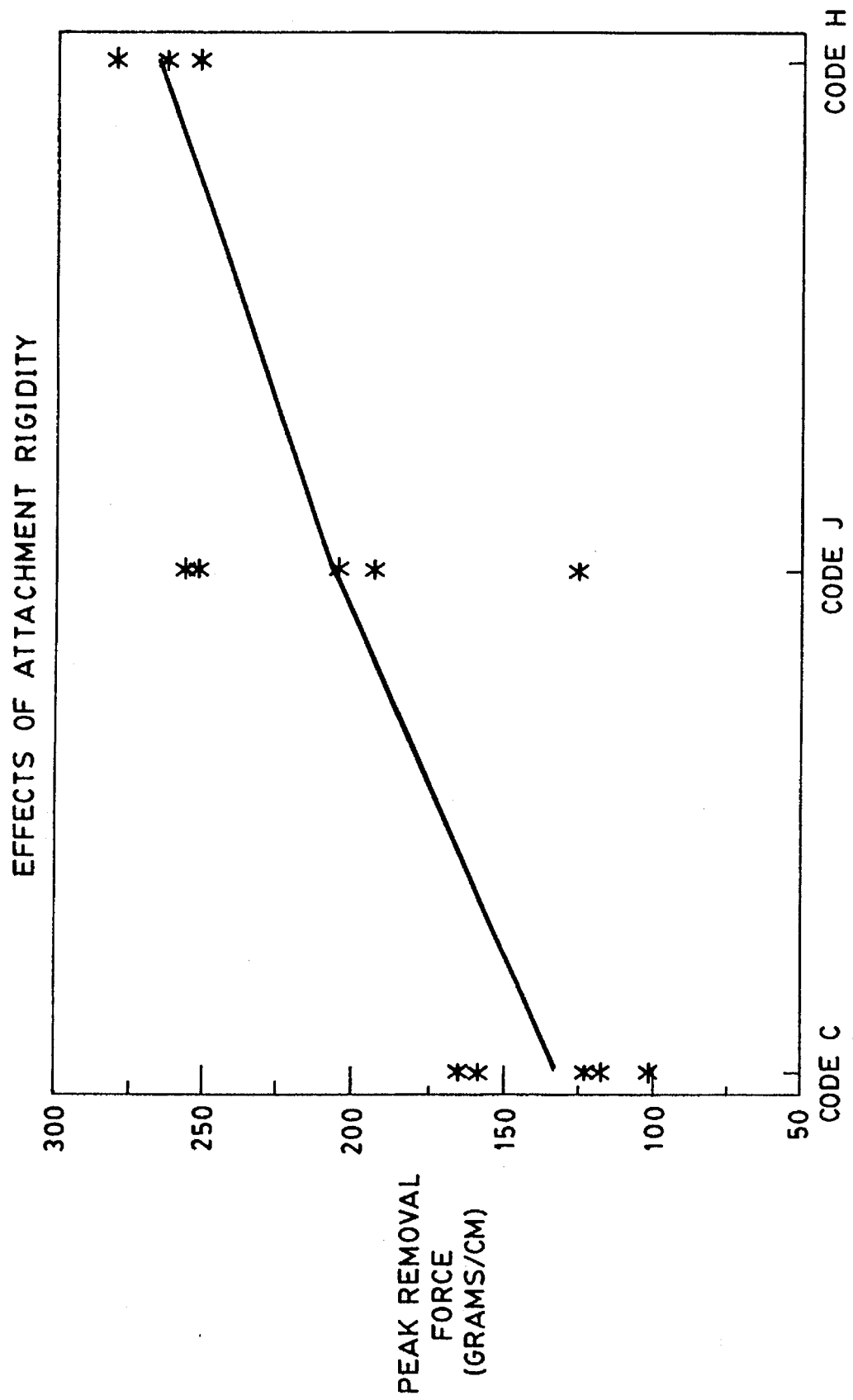

HIGH-PEEL TAB FASTENER

FIELD OF THE INVENTION

The present invention relates to fastening systems for disposable garments, such as caps, gowns, diapers, shoe covers, incontinence garments and the like. More particularly, the present invention relates to adhesive tape fastening systems and interlocking, mechanical-type fastening systems for disposable articles, such as gowns, diapers, incontinence garments and the like.

BACKGROUND OF THE INVENTION

Conventional disposable absorbent articles have typically employed adhesive fastening tapes for securing the article on a wearer. Such articles have also been constructed with interengaging mechanical fasteners, such as Velcro® type fasteners. Particular articles have included a fastening system which extends along substantially the entire length of an ear section of the article. Other fastening systems have included strips or segmented sections of adhesive. Still other systems have employed tapered fastening tabs where the adhesive area on the user's end is relatively wide at the longitudinally extending sides of the diaper, and is tapered to a more narrow width at its distal end. For example, see European Patent 0 233 704 B1 of H. Burkhard et al.

Conventional fastening systems, such as those described above, have not provided an adequate level of dynamic fit in combination with a neat tailored appearance and reliable securement. The conventional fastening systems have not provided a sufficient capability to move and adjust to accommodate the stresses and displacements caused by a moving wearer. As a result, the fastening systems have not provided desired levels of comfort and securement.

BRIEF DESCRIPTION OF THE INVENTION

Generally stated, the present invention provides a distinctive fastening tab which includes a fastener substrate having a construction-bond portion, a user-bond portion, a user-bond end section, a construction-bond end section, a pair of opposed side edge sections, a fastening surface and a user surface. A securing means connects to the fastening surface of the fastener substrate at least along the user-bond portion thereof, and a gripping member connects to the user surface at the user-bond portion of the fastener substrate. The gripping member has a distal end portion which is substantially free, and a base portion which is operably connected to the user surface of the fastener substrate. The gripping member is configured to intersect the fastener substrate at a location which is spaced from the construction-bond portion and is positioned between the construction-bond portion and the user-bond end section of the fastener substrate.

In a particular aspect of the invention, at least one fastening tab is configured for joining a fastener section of an article to a landing attachment section of the article. Another aspect of the invention can provide an absorbent article having a backsheet layer, a topsheet layer connected to the backsheet layer, and an absorbent body sandwiched between the backsheet and topsheet layers. The article includes a fastener section arranged for selectively joining to an appointed attachment section, and at least one fastening tab is configured for joining the fastener section to the attachment section.

In its various aspects, the distinctive fastening system of the present invention can advantageously provide an improved combination of neat appearance and dynamic fit. The closure stresses can be more efficiently distributed along the side sections of the article. In addition, the interconnected front and rear waistband sections of the article can more effectively adjust to accommodate movements of the wearer while maintaining a secure fastening therebetween. The distinctive configuration of the gripping member can help improve the reliability of the fastening system even when the fastening system is constructed to exhibit a relatively low peel-removal force. As a result, the various aspects of the fastening system of the invention can provide improved securement with fewer pop-opens, and can also provide improved fit, greater comfort, reduced irritation and reduced red marking of the wearer's skin.

BRIEF DESCRIPTION OF THE DRAWINGS

The present invention will be more fully understood and further advantages will become apparent when reference is made to the following detailed description of the invention and the drawings, in which:

FIG. 1A representatively shows a schematic, lateral cross-sectional view of the article shown in FIG. 1;

FIG. 1B representatively shows a schematic, longitudinal cross-sectional view of the article shown in FIG. 1;

FIG. 7 representatively shows a top plan view of a sample fastener tab prepared for testing to determine the removal force required to peel and pull it away from its associated attachment zone; and FIG. 7A representatively shows a schematic, side view of the sample fastener tab illustrated in FIG. 7;

FIG. 11 shows a table of data regarding the effects of the offset location of the gripping member;

FIG. 12 shows a table of data regarding the effects of the inset location of the gripping member;

FIG. 14 shows a table of data regarding the effects of the rigidity or stiffness of the fastener substrate portion located immediately above the securing means;

FIG. 17 shows a graph of the data regarding the effects of the stiffness of the fastener substrate portion located immediately above the securing means.

DETAILED DESCRIPTION OF THE INVENTION

The various embodiments of the invention will be described in the context of a disposable absorbent article, such as a disposable diaper. It is, however, readily apparent that the present invention could also be employed with other articles, such as caps, gowns, shoe covers, feminine care articles, incontinence garments and the like.

Typically, disposable articles are intended for limited use and are not intended to be laundered or otherwise cleaned for reuse. For example, a disposable diaper is discarded after it has become soiled by the wearer.

Figure 1:
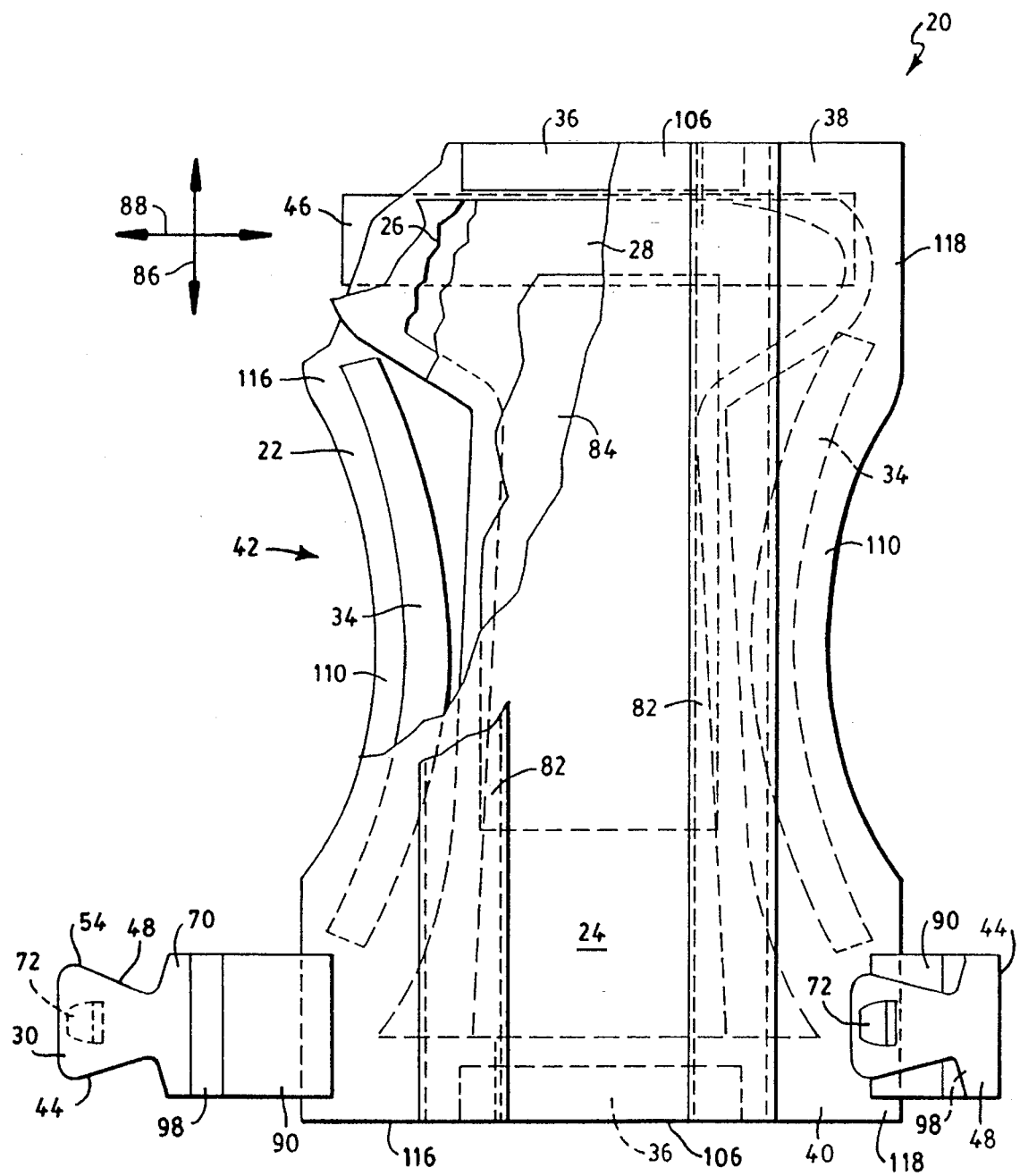
FIG. 1 representatively shows a partially cut-away, top plan view of a diaper article of the invention.
Figure 2:
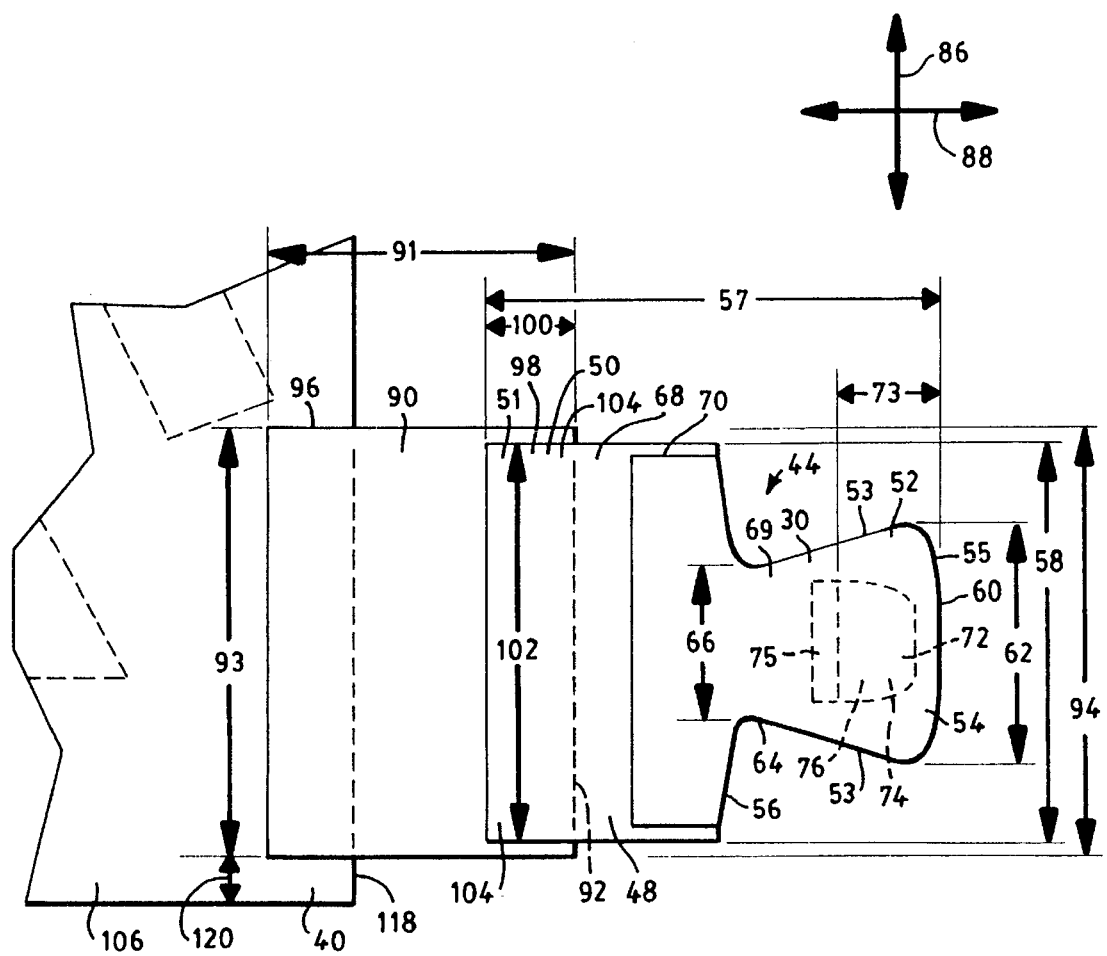
FIG. 2 representatively shows a plan view of a side panel and fastening tab assembly of the invention, where the fastener tab has a contoured user-bond portion with a narrowed intermediate section thereof.

With reference to FIGS. 1 and 2, a fastening tab 44 includes a fastener substrate 48 which has a construction-bond portion 50, a user-bond portion 52, a user-bond end edge section 60, a construction-bond end edge section 51, a pair of opposed side edge sections 53, a fastening surface 68, and a user surface 67. The shown construction-bond portion 50 is constructed to be affixed to an associated article, and the shown user-bond portion 52 is constructed to be selectively attached, as desired by a user. The illustrated user-bond portion 52 of the fastener substrate 48 extends laterally adjacent to the appointed construction-bond portion 50 of the fastener substrate. A securing means 54, such as provided by an adhesive or an appropriate hook-and-loop fastener component 30, connects to the fastening surface 68 of the fastener substrate 48 at least along the user-bond portion 52 of the fastener substrate, and a gripping member 72 connects to the user surface 67 at the user-bond portion 52 of the fastener substrate 48. The gripping member has a distal end portion 74 which is substantially free and a base portion 76 which operably connects to the user surface 67 of the fastener substrate 48. The gripping member is configured to intersect the fastener substrate 48 at a location which is spaced from the construction-bond portion 50 and is positioned between the construction-bond portion and the user-bond end section 60 of the fastener substrate.

In a particular aspect of the invention, at least one fastening tab 44 is constructed and arranged for selectively joining a fastener section of an article to an appointed landing attachment section of the article. For example, the article, such as diaper 20, can include an appointed fastener section, such as rear waistband portion 40, and an appointed landing attachment section, such as front waistband portion 38. At least one fastening tab 44 can be constructed and arranged for selectively and releasably joining the fastener section provided by the rear waistband portion to the landing attachment section provided by the front waistband portion.

Another aspect of the invention can further provide an absorbent article. For example, diaper 20 can further include a backsheet layer 22, a liquid permeable topsheet layer 24 connected to the backsheet layer, and an absorbent body 26 sandwiched between the backsheet and topsheet layers.

The representative disposable diaper 20 is shown in its fully extended condition with all of the elasticized gathers stretched out and removed. The article has a first waistband section, such as rear waistband section 40, a second waistband section, such as front waistband section 38, and an intermediate section 42 which interconnects the first and second waistband sections. The article includes a backsheet layer 22, and can include a pair of side panels 90, each of which extends laterally from opposed lateral ends of at least one waistband section of the diaper 20. In the shown embodiment, each side panel extends laterally from opposed lateral ends of the rear waistband section of the backsheet 22. Each of the side panels includes a terminal free end region 92 which has a predetermined length dimension 94 thereof. Each side panel also has a width 91 and a base length 93. A stress beam section 98 is connected to each of the side panels 90 along its free end region 92, and the stress beam section provides for a relatively high Gurley stiffness value, such as a Gurley stiffness value of at least about 20 mg. The stress beam section also has a length dimension 102 which is at least a significant substantial percentage, such as about 33 percent, of the length 94 of the free end region 92 of the side panel. A fastening tab 44 is connected to each of the stress beam sections and is arranged to extend laterally from each of the side panels 90 for securing the waistband sections of the article about a wearer during the use of the article. The fastening tab has a width dimension 57 and a length dimension 58. In particular configurations of the invention, the fastening tab can have a base length 58 which is about 100% of the length 102 of the stress beam section 98. In other configurations of the invention, the fastening tab can have a base length 58 which is not more than a selected limited percentage, such as about 90 percent, of the length 102 of the stress beam section 98.

Diaper 20 generally defines a longitudinally extending length dimension 86 and a laterally extending width dimension 88, as representatively shown in FIG. 1, and may have any desired shape, such as rectangular, I-shaped, a generally hourglass shape, or a T-shape. With the T-shape, the crossbar of the "T" may comprise the front waistband portion of the diaper or may alternatively comprise the rear waistband portion of the diaper.

Backsheet 22 can typically be located along an outer-side surface of the absorbent body 26 and may be composed of a liquid permeable material, but preferably comprises a material which is configured to be substantially impermeable to liquids. For example, a typical backsheet can be manufactured from a thin plastic film, or other flexible liquid-impermeable material. As used in the present specification, the term "flexible" refers to materials which are compliant and which will readily conform to the general shape and contours of the wearer's body. Backsheet 22 prevents the exudates contained in absorbent body 26 from wetting articles, such as bedsheets and overgarments, which contact diaper 20. In particular embodiments of the invention, backsheet 22 is a polyethylene film having a thickness of from about 0.012 millimeters (0.5 mil) to about 0.051 millimeters (2.0 mils). In the shown embodiment, the backsheet is a film having a thickness of about 1–1.5 mil. For example, the backsheet film can have a thickness of about 1.25 mil. Alternative constructions of the backsheet may comprise a woven or nonwoven fibrous web layer which has been totally or partially constructed or treated to impart the desired levels of liquid impermeability to selected regions that are adjacent or proximate the absorbent body. For example, the backsheet may include a gas-permeable, nonwoven fabric layer laminated to a polymer film layer. Other examples of fibrous, cloth-like backsheet materials can comprise a stretch thermal laminate material composed of a 0.6 mil (0.015 mm) thick polypropylene blown film and a 0.7 ounce per square yard (23.8 gsm) polypropylene spunbond material (2 denier fibers). A material of this type forms the outercover of a HUGGIES® Supreme diaper, which is commercially available from Kimberly-Clark Corporation. Backsheet 22 typically provides the outer cover of the article. Optionally, however, the article may comprise a separate outer cover component member which is in addition to the backsheet.

Backsheet 22 may alternatively be composed of a microporous, "breathable" material which permits gases, such as water vapor, to escape from absorbent body 26 while substantially preventing liquid exudates from passing through the backsheet. For example, the breathable backsheet may be composed of a microporous polymer film or a nonwoven fabric which has been coated or otherwise treated to impart a desired level of liquid impermeability. For example, a suitable microporous film can be a PMP-1 material, which is available from Mitsui Toatsu Chemicals, Inc., a company having offices in Tokyo, Japan; or an XK0-8044 polyolefin film available from 3M Company of Minneapolis, Minn. The backsheet may also be embossed or otherwise be provided with a matte finish to exhibit a more aesthetically pleasing appearance.

The size of backsheet 22 is typically determined by the size of absorbent body 26 and the particular diaper design selected. Backsheet 22, for example, may have a generally T-shape, a generally I-shape or a modified hourglass shape, and may extend beyond the terminal edges of absorbent body 26 by a selected distance, such as a distance of at least about 1.27 cm (about 0.5 in). In particular embodiments of the invention, backsheet can extend beyond the edges of absorbent body 26 by a distance within the range of about 1.3 centimeters to 2.5 centimeters (about 0.5 to 1.0 inch). Topsheet 24 presents a body-facing surface which is compliant, soft-feeling, and non-irritating to the wearer's skin. Further, topsheet 24 can be less hydrophilic than absorbent body 26, and is sufficiently porous to be liquid permeable, permitting liquid to readily penetrate through its thickness to reach the absorbent body. A suitable topsheet 24 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. Topsheet 24 is typically employed to help isolate the wearer's skin from liquids held in absorbent body 26.

Various woven and nonwoven fabrics can be used for topsheet 24. For example, the topsheet may be composed of a meltblown or spunbonded web of polyolefin fibers, and may also be a bonded-carded-web. The various fabrics can be composed of natural fibers, synthetic fibers or combinations thereof.

For the purposes of the present description, the term "nonwoven web" means a web of material which is formed without the aid of a textile weaving or knitting process. The term "fabrics" is used to refer to all of the woven, knitted and nonwoven fibrous webs.

The topsheet fabrics may be composed of a substantially hydrophobic material, and the hydrophobic material may optionally be treated with a surfactant or otherwise processed to impart a desired level of wettability and hydrophilicity. In a particular embodiment of the invention, topsheet 24 is a nonwoven, spunbond polypropylene fabric composed of about 2.8–3.2 denier fibers formed into a web having a basis weight of about 22 gsm and density of about 0.06 gm/cc. The fabric is surface treated with about 0.28% Triton X-102 surfactant.

In the shown embodiment of diaper 20, for example, topsheet 24 and backsheet 22 can be generally coextensive and have length and width dimensions which are generally larger than the corresponding dimensions of absorbent body 26. Topsheet 24 is associated with and superimposed on backsheet 22, thereby defining the periphery of diaper 20.

Topsheet 24 and backsheet 22 are connected or otherwise associated together in an operable manner. As used herein, the term "associated" encompasses configurations in which topsheet 24 is directly joined to backsheet 22 by affixing topsheet 24 directly to backsheet 22, and configurations wherein topsheet 24 is indirectly joined to backsheet 22 by affixing topsheet 24 to intermediate members which in turn are affixed to backsheet 22. Topsheet 24 and backsheet 22 can be affixed directly to each other in the diaper periphery by attachment means (not shown) such as adhesive bonds, sonic bonds, thermal bonds, pinning, stitching or any other attachment means known in the art, as well as combinations thereof. For example, a uniform continuous layer of adhesive, a patterned layer of adhesive, a sprayed pattern of adhesive or an array of separate lines, swirls or spots of construction adhesive may be used to affix topsheet 24 to backsheet 22. It should be readily appreciated that the above-described attachment means may also be employed to interconnect and assemble together the other component parts of the article.

Absorbent body 26 can comprise an absorbent pad composed of selected hydrophilic fibers and high-absorbency particles. The absorbent body is positioned and sandwiched between topsheet 24 and backsheet 22 to form diaper 20. The absorbent body has a construction which is generally compressible, conformable, non-irritating to the wearer's skin, and capable of absorbing and retaining liquid body exudates. It should be understood that, for purposes of this invention, the absorbent body may comprise a single, integral piece of material, or alternatively, may comprise a plurality of individual separate pieces of material which are operably assembled together.

Various types of wettable, hydrophilic fibrous material can be used to form the component parts of absorbent body 26. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers; and synthetic fibers composed of a nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed.

As used herein, the term "hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System. When measured with this system in accordance with the procedure described in detail herein below, fibers having contact angles less than 90° are designated "wettable", while fibers having contact angles greater than 90° are designated "nonwettable".

Absorbent body 26 can comprise a matrix of hydrophilic fibers, such as a web of cellulosic fluff, mixed with particles of high-absorbency material. In particular arrangements, absorbent body 26 may comprise a mixture of superabsorbent hydrogel-forming particles and synthetic polymer meltblown fibers, or a mixture of superabsorbent particles with a fibrous coform material comprising a blend of natural fibers and/or synthetic polymer fibers. The superabsorbent particles may be substantially homogeneously mixed with the hydrophilic fibers, or may be nonuniformly mixed. For example, the concentrations of superabsorbent particles may be arranged in a non-step-wise gradient through a substantial portion of the thickness (z-direction) of the absorbent structure, with lower concentrations toward the bodyside of the absorbent body and relatively higher concentrations toward the outerside of the absorbent structure. Suitable z-gradient configurations are described in U.S. Pat. No. 4,699,823, issued Oct. 13, 1987 to Kellenberger et al., the entire disclosure of which is incorporated herein by reference in a manner that is consistent (not in conflict) with the present description. Alternatively, the concentrations of superabsorbent particles may be arranged in a non-step-wise gradient, through a substantial portion of the thickness (z-direction) of the absorbent structure, with higher concentrations toward the bodyside of the absorbent body and relatively lower concentrations toward the outerside of the absorbent structure. The superabsorbent particles may also be arranged in a generally discrete layer within the matrix of hydrophilic fibers. In addition, two or more different types of superabsorbent may be selectively positioned at different locations within or along the fiber matrix.

The high-absorbency material may comprise absorbent gelling materials, such as superabsorbents. Absorbent gelling materials can be natural, synthetic and modified natural polymers and materials. In addition, the absorbent gelling materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic absorbent gelling material polymers include the alkali metal and ammonium salts of poly(acrylic acid) and poly (methacrylic acid), poly(acrylamides), poly(vinyl ethers), maleic anhydride copolymers with vinyl ethers and alpha-olefins, poly(vinyl pyrrolidone), poly(vinylmorpholinone), poly(vinyl alcohol), and mixtures and copolymers thereof. Further polymers suitable for use in the absorbent body include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum and the like. Mixtures of natural and wholly or partially synthetic absorbent polymers can also be useful in the present invention. Other suitable absorbent gelling materials are disclosed by Assarsson et al. in U.S. Pat. No. 3,901,236, issued Aug. 26, 1975. Processes for preparing synthetic absorbent gelling polymers are disclosed in U.S. Pat. No. 4,076,663, issued Feb. 28, 1978 to Masuda et al. and U.S. Pat. No. 4,286,082, issued Aug. 25, 1981 to Tsubakimoto et al.

Synthetic absorbent gelling materials typically are xerogels which form hydrogels when wetted. The term "hydrogel", however, has commonly been used to also refer to both the wetted and unwetted forms of the material.

As mentioned previously, the high-absorbency material used in absorbent body 26 is generally in the form of discrete particles. The particles can be of any desired shape, for example, spiral or semi-spiral, cubic, rod-like, polyhedral, etc. Shapes having a large greatest dimension/smallest dimension ratio, like needles, flakes, and fibers, are also contemplated for use herein. Conglomerates of particles of absorbent gelling material may also be used in absorbent body 26.

Desired for use are particles having an average size of from about 20 microns to about 1 millimeter. "Particle size" as used herein means the weighted average of the smallest dimension of the individual particles.

The hydrophilic fibers and high-absorbency particles can be configured to form an average composite basis weight which is within the range of about 400–900 gsm. In certain aspects of the invention, the average composite basis weight is within the range of about 500–800 gsm, and preferably is within the range of about 550–750 gsm to provide desired performance.

To improve the containment of the high-absorbency material, absorbent body 26 can include an improved overwrap, such as wrap sheet 28, placed immediately adjacent and around absorbent body 26. The wrap sheet is preferably a layer of absorbent material which covers the major bodyside and outerside surfaces of the absorbent body, and preferably encloses substantially all of the peripheral edges of the absorbent body to form a substantially complete envelope thereabout. Alternatively, the wrap sheet can provide an absorbent wrap which covers the major bodyside and outerside surfaces of the absorbent body, and encloses substantially only the lateral side edges of the absorbent body. Accordingly, both the linear and the inwardly curved portions of the lateral side edges of the wrap sheet would be closed about the absorbent body. In such an arrangement, however, the end edges of the wrap sheet may not be completely closed around the end edges of the absorbent body at the waistband regions of the article.

For example, the complete wrap sheet 28, or at least the bodyside layer of the wrap sheet, may comprise a meltblown web composed of meltblown fibers, such as meltblown polypropylene fibers. Another example of absorbent wrap 28 may comprise a low porosity cellulosic web, such as a tissue composed of an approximately 50/50 blend of hardwood/softwood fibers.

Absorbent wrap 28 may comprise a multi-element wrapsheet which includes a separate bodyside wrap layer and a separate outerside wrap layer, each of which extends past all or some of the peripheral edges of absorbent body 26. Such a configuration of the wrap sheet can, for example, facilitate the formation of a substantially complete sealing and closure around the peripheral edges of absorbent body 26. In the back waistband portion of the illustrated diaper, the absorbent wrap may also be configured to extend an increased distance away from the periphery of the absorbent body to add opacity and strength to the back side-sections of the diaper. In the illustrated embodiment, the bodyside and outerside layers of absorbent wrap 28 extend at least about ½ inch beyond the peripheral edges of the absorbent body to provide an outwardly protruding, flange-type bonding area over which the periphery of the bodyside portion of the absorbent wrap may be completely or partially connected to the periphery of the outerside portion of the absorbent wrap.

The bodyside and outerside layers of wrap sheet 28 may be composed of substantially the same material, or may be composed of different materials. For example, the outerside layer of the wrap sheet may be composed of a relatively lower basis weight material having a relatively high porosity, such as a wet strength cellulosic tissue composed of softwood pulp. The bodyside layer of the wrap sheet may comprise one of the previously described wrap sheet materials which has a relatively low porosity. The low porosity bodyside layer can better prevent the migration of superabsorbent particles onto the wearer's skin, and the high porosity, lower basis weight outerside layer can help reduce costs.

Diaper 20 can also include a surge management layer 84 which helps to decelerate and diffuse surges of liquid that may be introduced into the absorbent body of the article. In the illustrated embodiment, for example, surge layer 84 can be located on an inwardly facing body side surface of topsheet layer 24. Alternatively, surge layer 84 may be located adjacent to an outer side surface of topsheet 24. Accordingly, the surge layer would then be interposed between topsheet 24 and absorbent body 26. Examples of suitable surge management layers 84 are described in U.S. patent application Ser. No. 206,986 of C. Ellis and D. Bishop, entitled FIBROUS NONWOVEN WEB SURGE LAYER FOR PERSONAL CARE ABSORBENT ARTICLES AND THE LIKE, filed Mar. 4, 1994 (Attorney docket No. 11,256); and U.S. patent Application Ser. No. 206,069 of C. Ellis and R. Everett, entitled IMPROVED SURGE MANAGEMENT FIBROUS NONWOVEN WEB FOR PERSONAL CARE ABSORBENT ARTICLES AND THE LIKE, filed Mar. 4, 1994 (Attorney docket No. 11,387); the entire disclosures of which are hereby incorporated by reference in a manner that is consistent (not contradictory) herewith.

Leg elastic members 34 are located in the lateral side margins 110 of diaper 20 and are arranged to draw and hold diaper 20 against the legs of the wearer. The elastic members are secured to diaper 20 in an elastically contractible condition so that in a normal under strain configuration, the elastic members effectively contract against diaper 20. The elastic members can be secured in an elastically contractible condition in at least two ways, for example, the elastic members may be stretched and secured while diaper 20 is in an uncontracted condition. Alternatively, diaper 20 may be contracted, for example, by pleating, and the elastic members secured and connected to diaper 20 while the elastic members are in their relaxed or unstretched condition. Still other means, such as heat-shrink elastic material, may be used to gather the garment.

In the embodiment illustrated in FIG. 1, leg elastic members 34 extend essentially along the complete length of the intermediate crotch region 42 of diaper 20. Alternatively, elastic members 34 may extend the entire length of diaper 20, or any other length suitable providing the arrangement of elastically contractible lines desired for the particular diaper design.

Elastic members 34 may have any of a multitude of configurations. For example, the width of the individual elastic members 34 may be varied from 0.25 millimeters (0.01 inches) to 25 millimeters (1.0 inches) or more. The elastic members may comprise a single strand of elastic material, or may comprise several parallel or non-parallel strands of elastic material, or may be applied in a rectilinear or curvilinear arrangement. Where the strands are non-parallel, two or more of the strands may intersect or otherwise interconnect within the elastic member. The elastic members may be affixed to the diaper in any of several ways which are known in the art. For example, the elastic members may be ultrasonically bonded, heat and pressure sealed using a variety of bonding patterns, or adhesively bonded to diaper 20 with sprayed or swirled patterns of hotmelt adhesive.

In particular embodiments of the invention, leg elastic members 34 may comprise a carrier sheet (not shown) to which are attached a grouped set of elastics composed of a plurality of individual elastic strands 39. The elastic strands may intersect or be interconnected, or be entirely separated from each other. The carrier sheet may, for example, comprise a 0.002 cm thick film of unembossed polypropylene material. The elastic strands can, for example, be composed of Lycra elastomer available from DuPont, a business having offices in Wilmington, Del. Each elastic strand is typically within the range of about 470–1500 decitex (dtx), and may be about 940–1050 dtx. In particular embodiments of the invention, for example, three or four strands can be employed for each elasticized legband.

In addition, leg elastics 34 may be generally straight or optionally curved. For example, the curved elastics can be inwardly bowed toward the longitudinal centerline of the diaper with the innermost point (or apex, relative to the cross-direction of the article) of the set of curved elastic strands positioned approximately 0.75–1.5 inches inward from the outer most edge of the set of elastic strands. In particular arrangements, the curvature of the elastics may not be configured or positioned symmetrically relative to the lateral centerline of the diaper. The curved elastics may have an inwardly bowed and outwardly bowed, reflex-type of curvature, and the length-wise center of the elastics may optionally be offset by a selected distance toward either the front or rear waistband of the diaper to provide desired fit and appearance. In particular embodiments of the invention, the innermost point (apex) of the set of curved elastics can be offset towards the front or rear waistband of the diaper, and the outwardly bowed reflexed-portion can be positioned toward the diaper front waistband.

In the shown embodiment, diaper 20 includes a waist elastic 36 positioned in the longitudinal margins of either or both of front waistband 38 and rear waistband 40. The waist elastics may be composed of any suitable elastomeric material, such as an elastomer film, an elastic foam, multiple elastic strands, an elastomeric fabric or the like. For example, suitable elastic waist constructions are described in U.S. Pat. No. 4,916,005 to Lippert et al., the entire disclosure of which is hereby incorporated by reference in a manner that is consistent (not contradictory) herewith.

Diaper 20 can also include a pair of elasticized containment flaps 82 which extend longitudinally along the length dimension 86 of the diaper. The containment flaps are typically positioned laterally inboard from leg elastics 34, and substantially symmetrically placed on each side of the lengthwise, longitudinal centerline of the diaper. Examples of suitable containment flap constructions are described in U.S. Pat. No. 4,704,116, issued Nov. 3, 1987, to K. Enloe, the entire disclosure of which is hereby incorporated by reference in a manner that is consistent herewith. The containment flaps may be composed of a wettable or a non-wettable material, as desired. In addition, the containment flap material may be substantially liquid-impermeable, permeable to gas or permeable to both gas and liquid. Other suitable containment flap configurations are described in U.S. patent application Ser. No. 206,816 of R. Everett et al., filed Mar. 4, 1994 and entitled ABSORBENT ARTICLE HAVING AN IMPROVED SURGE MANAGEMENT (Attorney docket No. 11,375), the disclosure of which is hereby incorporated by reference in a manner that is consistent herewith.

In an optional, alternative embodiment of the invention, diaper 20 may include elasticized waist flaps, such as those described in U.S. Pat. No. 4,753,646, issued Jun. 28, 1988, to K. Enloe, the entire disclosure of which is hereby incorporated by reference in a manner that is consistent herewith. Similar to the construction of the containment flaps, the waist flaps may be composed of a wettable or non-wettable material, as desired. The waist flap material may be substantially liquid-impermeable, permeable to gas, or permeable to both gas and liquid.

Absorbent article structures suitable for use with the present invention are described in U.S. Pat. No. 5,192,606, issued Mar. 9, 1993 to D. Proxmire et al., and entitled "ABSORBENT ARTICLE HAVING A LINER WHICH EXHIBITS IMPROVED SOFTNESS AND DRYNESS, AND PROVIDES FOR RAPID UPTAKE OF LIQUID" (Attorney Docket No. 9932), the entire disclosure of which is hereby incorporated by reference in a manner that is consistent with the present specification. Other absorbent article structures suitable for use with the present invention are described in U.S. patent application Ser. No. 07/757,760; "THIN ABSORBENT ARTICLE HAVING RAPID UPTAKE OF LIQUID"; of W. Hanson et al. (Attorney Docket No. 9922), the entire disclosure of which is hereby incorporated by reference in a manner that is consistent herewith.

To provide a refastenable fastening system, diaper 20 can include a supplemental landing zone patch 46, which provides a target zone for receiving a releasable attachment of tape fasteners 44 thereon. In the illustrated embodiment of the invention, landing zone patch 46 is positioned on the outward surface of backsheet 22 and is located on the front waistband portion 38 of the diaper. In an adhesive fastening system, for example, landing zone patch 46 can be constructed of a suitable material, such as polypropylene, polyester, or the like, and is configured and arranged to accept a secure adhesion of tape fasteners 44. In addition, the landing zone patch and the tape fasteners are cooperatively constructed and arranged to provide a releasable adhesion which allows the tape fastener to be removed from the landing zone patch for repositioning and re-adhesion without tearing or excessively deforming the material of backsheet 22. For example, a suitable tape landing zone construction is described in U.S. Pat. No. 5,024,672, issued Jun. 18, 1991, to L. Widlund. A further construction of a tape landing zone patch is described in U.S. Pat. No. 4,753,649 issued to Pazdernik, the entire disclosure of which is hereby incorporated by reference in a manner that is consistent herewith.

In a cohesive fastening system, landing zone 46 can include a cohesive material which is configured and arranged to provide a secure attachment with the cooperative cohesive material located on the fastening surface of the fastener tabs 44. A configuration which employs a releasable, interengaging mechanical fastening system can locate a first portion of the mechanical fastener on the landing zone 46 and a second, cooperating portion of the mechanical fastener on the fastener tab 44. For example, with a hook-and-loop fastener, the hook material 30 can be operably connected to the fastener tabs 44 and the loop material can be operably connected to the landing zone 46. Alternatively, the loop material can be operably connected to the fastener tabs 44 and the hook material can be operably connected to the landing zone 46.

In various embodiments of the invention, a tape fastener tab 44 can be located at either or both of lateral end regions 116 and 118 of either or both of waistbands 38 and 40. The representatively shown embodiment has the fasteners tabs 44 located at the distal side edges of rear waistband 40.

Figure 5:
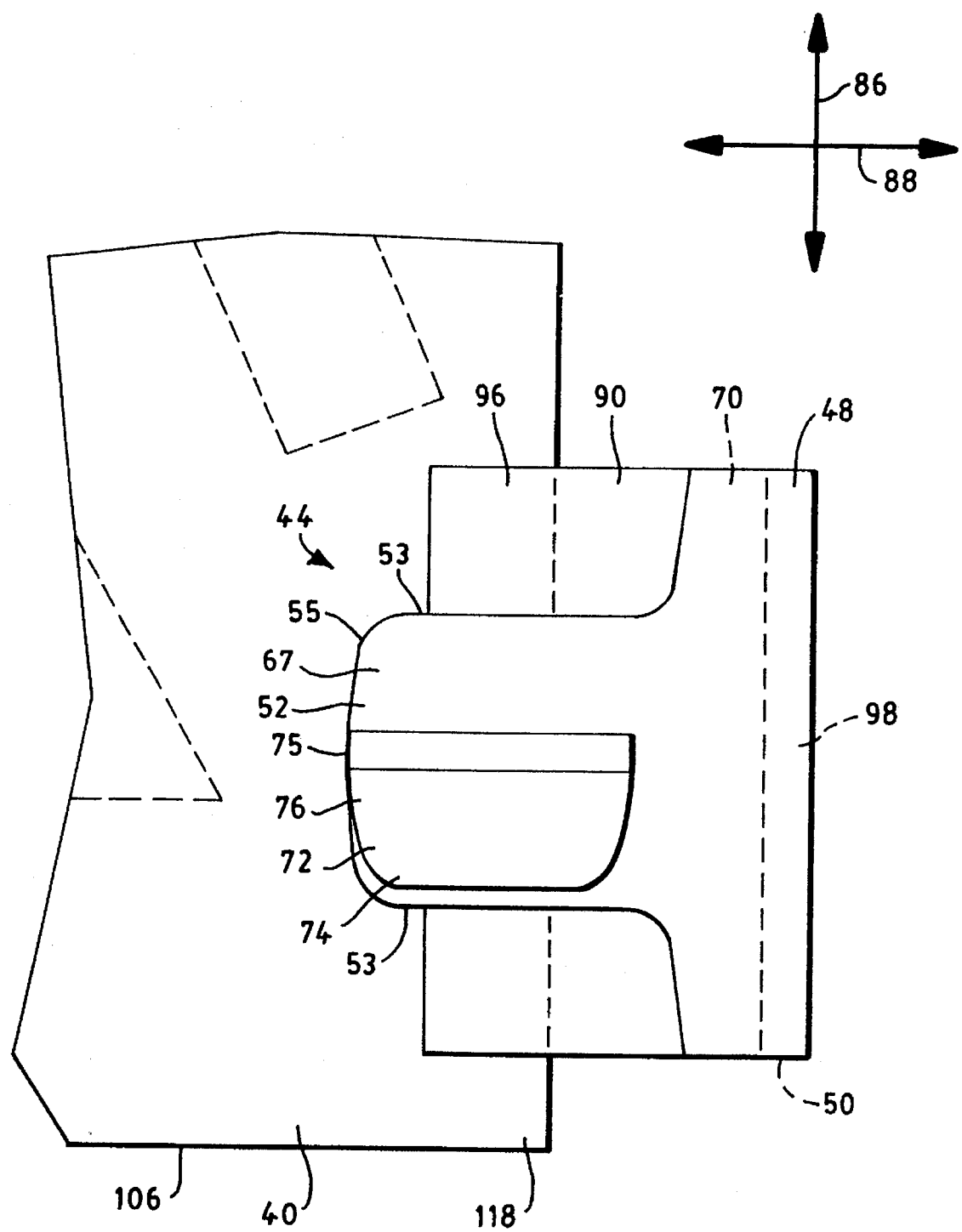
FIG. 5 representatively shows a plan view of a side panel and a folded-over fastening tab assembly of the invention, where the fastening tab has a generally rectangular user-bond portion and has a gripping member which intersects the fastener substrate along a generally laterally extending line.

With reference to FIGS. 1 and 5, each side panel 90 extends laterally from the opposed lateral ends of at least one waistband portion of backsheet 22, such as rear waistband portion 40, to provide terminal side sections of the article. In addition, each side panel can substantially span from a laterally extending, terminal waistband edge 106 to approximately the location of a corresponding leg opening section of the diaper. Diaper 20, for example, has a laterally opposed pair of leg openings formed by appointed, medial sections of the shown pair of longitudinally extending, side edge regions 110 (FIG. 1).

In the various configurations of the invention, the side panels may be integrally formed with a selected diaper component. For example, side panels 90 can be integrally formed from the layer of material which provides backsheet layer 22, or may be integrally formed from the material employed to provide topsheet 24. In alternative configurations, the side panels 90 may be provided by one or more separate members that are connected to backsheet 22, to topsheet 24, in between the backsheet and topsheet, or combinations thereof.

In particular aspects of the invention, each of the side panels 90 may be formed from a separate piece of material which is then suitably assembled and attached to the selected front and/or rear waistband portion of the diaper article. In the illustrated embodiments of the invention, for example, each side panel 90 is attached to the rear waistband portion of backsheet 22 along a side panel attachment zone 96, and can be operably attached to either or both of the backsheet and topsheet components of the article. The side panels extend laterally to form a pair of opposed waist-flap sections of the diaper, and are attached with suitable connecting means, such as adhesive bonding, thermal bonding, ultrasonic bonding, clips, staples, sewing or the like.

Side panels 90 may be composed of a substantially non-elastomeric material, such as polymer films, woven fabrics, nonwoven fabrics or the like, as well as combinations thereof. In particular aspects of the invention, side panels 90 are composed of a substantially elastomeric material, such as a stretch-bonded-laminate (SBL) material, a neck-bonded-laminate (NBL) material, an elastomeric film, an elastomeric foam material, or the like. For example, suitable meltblown elastomeric fibrous webs for forming side panels 90 are described in U.S. Pat. No. 4,663,220, issued May 5, 1987 to T. Wisneski et al., the entire disclosure of which is hereby incorporated by reference. Examples of composite fabrics comprising at least one layer of nonwoven textile fabric secured to a fibrous elastic layer are described in European Patent Application EP No. 0 110 010 published on Apr. 8, 1987 with the inventors listed as J. Taylor et al., the entire disclosure of which is hereby incorporated by reference. Examples of NBL materials are described in U.S. Pat. No. 5,226,992, issued Jul. 13, 1993 to Mormon, the entire disclosure of which is hereby incorporated by reference.

As previously mentioned, various suitable constructions can be employed to attach the side panels 90 to the selected waistband portions of the article. Where the side panels are composed of an elastomeric material, for example, suitable constructions for securing a pair of elastomeric, stretchable members to the lateral, side portions of an article to extend laterally outward beyond the opposite side regions of the outer cover and liner components of an article can be found in U.S. Pat. No. 4,938,753, issued Jul. 3, 1990 to P. VanGompel et al., the entire disclosure of which is hereby incorporated by reference in a manner that is consistent herewith.

In other aspects of the invention, side panels 90 can be composed of a material having a Gurley stiffness value of not more than about 10,000 milligrams (mg). Optionally, the side panel material has a stiffness value of not more than about 2,000 mg, and optionally has a stiffness value of not more than about 200 mg.

In further aspects of the invention, side panels 90 can be composed of a material having a Gurley stiffness value of not less than about 1 mg. Alternatively, the side panel material has a stiffness value of not less than about 4 mg, and optionally has a stiffness value of not less than about 8 mg.

In the various configurations of the invention the desired Gurley stiffness value can be exhibited with respect to the width dimension, or with respect to both the width and length dimensions of the side panel.

In particular configurations of the invention where side panels 90 are composed of an elastomeric material, the elastomeric side panels are composed of a material which can provide an elongation at peak load of at least about 30 percent when subjected to a tensile force load of 0.33 pounds per lineal inch of the sample dimension that is measured perpendicular to the direction of the applied load (about 0.58 Newtons/cm). Alternatively, the elastomeric side panel material can provide an elongation of at least about 100%, and optionally can provide an elongation of at least about 300% to provide desired performance.

In conventional fastening systems, the fastening stress is applied to the construction bond between fastening tab 44 and the side sections of rear waistband 40 substantially across the base length 58 of the fastening tab. As a result, relatively low levels of stress are applied to the regions of the ear sections that are longitudinally adjacent to the side edges of the fastening tab. As a result, the longitudinally adjacent regions tend to wrinkle and curl away from the body of the wearer. The wrinkling and curling can be unsightly and can create gaps along the waistband and along the leg opening region of the diaper through which waste materials may leak from the diaper. Attempts to address this problem have employed complex fastening systems which extend along substantially the entire free edge length of the ear sections of the article. Other attempts to address this problem have employed multiple fastening tapes or a large, wide fastening tab. The wide fastening tabs or tapered fastening tabs have transmitted excessive stresses to the user-bond securement section of the fastening system. Such stresses can tend to undesirably disconnect the user-bond portion of the fastening system when the wearer shifts and moves about. In addition, such configurations may not sufficiently conform and adjust to the movements of the wearer, and can result in excessive irritation of the wearer's skin.

To help address the problems associated with conventional fastening systems such as those described above, the present invention can advantageously include a distinctive reinforcement, stress beam section 98. The stress beam can disperse and dissipate the fastening forces across the length of each side panel 90. In addition, the stress beam section can provide for a sufficient stiffening and reinforcement of its associated waistband section to help prevent undesired and excessive wrinkling, necking-down or folding-over of the lateral end of the waistband or side panel during the use of the article.

In the various configurations of the invention, stress beam section 98 can be integrally formed from the same material employed to form the side panel 90 associated therewith. For example, a portion of the free end of a side panel may be doubled over one or more times along longitudinally extending fold lines to generate an operable stress beam section. Alternatively, the stress beam section can be provided by densifying or embossing a selectively sized and shaped region of side panel 90 to an extent which provides operable levels of strength and stiffness.

In other arrangements of the invention, stress beam section 98 can include a stiffening or reinforcement member provided by a selectively shaped and sized region of material which is integrally formed with fastening tab substrate 48. Alternatively, the stress beam section can include a separate stiffening or reinforcement member which is appropriately configured, and is assembled to the free end region of the side panel. For example, the stress beam section can be provided for by a suitably sized and shaped piece of material attached to a suitable surface of each side panel 90, such as an inward bodyside surface of each panel. The material may be composed of a polymer film, a nonwoven fabric, a woven fabric or the like, as well as combinations thereof. In a particular configuration, the stress beam section can include a stiffening member composed of the material employed to construct a release tape and/or the fastening tab substrate 48. Alternative configurations of the stress beam section can be provided for by a longitudinally extending region of the securing means 54, such as a laterally inboard section 70 of a securement substrate layer 78 which may be employed as a part of the hook material 30 (FIG. 2). In the various configurations of the invention the stress beam section can be substantially non-extensible and/or substantially non-elastomeric.

Figure 2A:
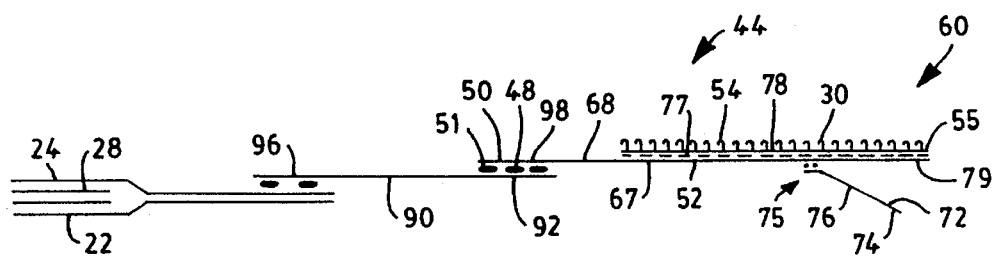
FIG. 2A representatively shows a schematic, lateral side view of the side panel and fastening tab assembly representatively shown in FIG. 2.

With reference to FIGS. 2 and 2A, the stress beam section 98 can be operably connected to each side panel 90 along the free end region 92 of the side panel with suitable attaching means, such as adhesive bonding, thermal bonding, ultrasonic bonding, clips, staples, sewing or the like. The stress beam section has a laterally extending, cross-directional width dimension 100 and a longitudinally extending length dimension 102. To obtain desired performance, it can be advantageous to position stress beam section 98 at a medial location along the length of side panel 90. In the shown embodiment, for example, the stress beam section is substantially centered along the longitudinal length of the free end section of the side panel.

In a particular aspect of the invention, the stress beam section length 102 is at least about 33 percent of the length 94 of the free end region 92 of side panel 90. Alternatively, the stress beam section length is at least about 80 percent of the free end region length 94 of the side panel, and optionally is about 100 percent of the free end region length to provide desired benefits. Particular configurations of the invention can include a stress beam having a length of up to about 125% of the free end region length 94 of the side panel to provide desired performance. In other aspects of the invention, the stress beam section length is not less than about 1.25 cm. Alternatively, the stress beam section length is not less than about 2.5 cm, and optionally is not less than about 5 cm to provide improved performance. In further aspects of the invention, the stress beam section length is not more than about 15 cm. Alternatively, the stress beam section length is not more than about 13 cm, and optionally is not more than about 10 cm to provide desired performance.

In the various configurations of the invention, the stress beam section width 100 is not less than about 0.1 cm. Alternatively, the stress beam section width is not less than about 0.5 cm, and optionally is not less than about 1.0 cm to provide improved performance. In other aspects of the invention, the stress beam section width is not more than about 10 cm. Alternatively, the stress beam section width is not more than about 5 cm, and optionally is not more than about 2.5 cm to provide desired performance.

An arrangement of the invention can be configured to employ a separate piece of material which operatively forms a member that overlaps the material of side panel 90 to provide for the desired stress beam section 98. For example, substantially 100% of the width of the separate beam member can be arranged to overlap the material of side panel 90. Optionally, less than 100% of the width of the beam member can be arranged to overlap the material of the side panel.

In particular aspects of the invention, stress beam section 98 extends along the longitudinal length of side panel 90 to be substantially coterminous with the laterally extending waistband edge 106 of the article. In the illustrated embodiment, fastening tab 44 is approximately centered along the length of stress beam section 98. Alternatively, the location of fastening tab 44 may be asymmetrically inset longitudinally of the diaper by a selected distance away from the lengthwise center of stress beam section 98. In particular aspects of the invention, fastening tab 44 may be spaced from waistband edge 106 by a spacing distance 120 which is not more than about 6 centimeters. Alternatively the spacing is not more than about 4 centimeters, and optionally is not more than about 2 centimeters to provide improved benefits. In further aspects of the invention, the edge of fastening tab 44 may be arranged to substantially coincide with waistband edge 106 to provide improved performance.

In the various aspects of the invention, stress beam section 98 can provide for a rigidity, stiffness value which is greater than the stiffness value of side panel 90. More particularly, the stress beam section can advantageously be composed of a material which provides for a Gurley stiffness value of the stress beam of at least about 20 mg, and in desired configurations, can provide for a Gurley stiffness value of at least about 100 mg. Alternatively, the material of stress beam section 98 provides for a stiffness value of at least about 200 mg, and optionally, provides for a stiffness value of at least about 400 mg.

If the stress beam section is too stiff, however, it can cause excessive irritation and red-marking of the wearer's skin. Accordingly, further aspects of the invention can be configured with the material of stress beam section 98 providing for a Gurley stiffness value of the stress beam not more than about 50,000 mg. Alternatively, the stress beam material can provide for a stress beam stiffness value of not more than about 10,000 mg, and optionally can provide for a stiffness value of not more than about 1,000 mg to provide desired performance.

In the various configurations of the invention the desired Gurley stiffness value can be exhibited with respect to the length dimension, or with respect to both the width and length dimensions of the stress beam section.

In further aspects of the invention, the assembled stress beam section 98, relative to its associated side panel 90 connected thereto, exhibits a stiffness ratio of at least about 5:1. Alternatively, this stiffness ratio is at least about 10:1, and optionally is at least about 30:1. In other aspects of the invention, stress beam section 98 and its associated side panel 90 have a stiffness ratio of not more than about 50,000:1. Alternatively, the stiffness ratio is not more than about 5,000:1, and optionally is not more than about 500:1 to provide desired benefits.

With reference to FIGS. 2 and 2A, the stress beam 98 can be provided by a laminated region composed of side panel 90 and a laterally inboard, end section of fastener substrate 48. Optionally, the stress beam can include a laterally inboard section of hook material 30. More particularly, hook material 30 can include a securement substrate portion 78 which is operably affixed to fastener substrate 48 with a suitable substrate attachment 77. The substrate attachment has a laterally terminal end 55, and the securement substrate includes a laterally inboard section 70.

It should be appreciated that the stress beam system can be modified with further constructions and arrangements. For example, suitable configurations of the stress beam fastener system are described in U.S. Patent Application Ser. No. 08/168,615 of T. Roessler et al., entitled DYNAMIC FITTING DIAPER, filed Dec. 16, 1993 (attorney docket No. 10,961), the entire disclosure of which is incorporated by reference in a manner that is consistent herewith.

A fastening means, such as fastening tape tab 44 is operably connected to each of the side panels 90. In particular configurations, the juncture section along which fastening tab 44 intersects the terminal side edge of panel 90 may optionally provide a relatively narrowed panel juncture region. The connection may be accomplished with suitable attaching means, such as adhesive bonding, thermal bonding, ultrasonic bonding, clips, staples, sewing or the like. Alternatively, the fastening tab substrate may be integrally formed from the material employed to form stress beam section 98. In optional configurations, the fastening tab may be directly or indirectly connected to the stress beam section 98 associated with the respective side panel. For example, the fastening tab 44 may indirectly connect to its associated stress beam 98 by way of an intervening section of side panel 90.

In the illustrated embodiments of the invention, the components of the fastening means cooperate to secure the front and rear waistband portions of the article about a wearer. In particular, the rear waistband section of the shown embodiment overlaps the front waistband section of the article and the fastening means operably attaches to appointed regions of the front waistband portion. With reference to FIGS. 2 and 2A, fastening tab 44 has a longitudinally extending length dimension and a laterally extending width dimension. In addition, the fastening tab has a base section 56, a user bond end section 60 and an intermediate section 64 which interconnects the base and end sections. Base section 56 has a longitudinal length dimension 58, end section 60 has a longitudinal length dimension 62, and intermediate section 64 has a longitudinal length dimension 66.

In particular aspects of the invention, fastening tab 44 has, along its respective panel juncture region, a base length 58 which is not less than about 50 percent of the length 102 of stress beam section 98. Alternatively, the fastening tab base length is not less than about 80 percent of the stress beam section length, and optionally is not less than about 90 percent of the stress beam section length to provide desired performance. Accordingly, when the fastening means is employed to secure the article on the wearer, the end sections 104 of the stress beam section may or may not be further attached to the front waistband of the article by the operation of securing the article on the wearer. As a result, the unattached end sections 104 can slide, bend and otherwise move relative to the secured portions of the article without excessively disturbing the securing attachment between the user bond section of the fastening tab and the appointed securement zone of the article.

In the embodiment representatively shown in FIGS. 2 and 2A, length 58 of the base section 56 of fastening tab 44 is relatively larger than the length 66 of the fastening tab intermediate section 64. Alternatively, however, base length 58 may be equal to or less than the intermediate section length 66. In either case, the construction of the fastening system of the invention can provide a seam section 69 the fastening tab which is positioned between stress beam section 98 and the user bond section 52 of the fastening tab. As determined when the fastening tab in its relaxed and substantially untensioned condition, the tab seam section generally represents the narrowest region of the fastening tab with respect to those portions of the fastening tab that are spaced from the terminal end sections of the tab. Seam section 69 can advantageously provide a relatively more flexible pivot region which can facilitate a freer, less restricted relative movement between the stress beam portion of the fastening system and user bond portion of the fastening tab. As a result, the stress beam 98 can operate to help maintain the desired waistband appearance and good fit during the movements of the wearer, and the user bond section 52 can maintain a more reliable securement with less occurrence of undesired pop-opens. The seam section can help isolate the user bond section of the fastening system from the self-adjusting movements of the side panels 90 and the stress beam sections of the fastening system. In the shown embodiment, the seam section 69 is composed of a substantially non-extensible and substantially non-elastomeric material, but may alternatively be composed of an elastomeric material which is operably assembled or otherwise incorporated into the fastening tab structure.

Figure 3:
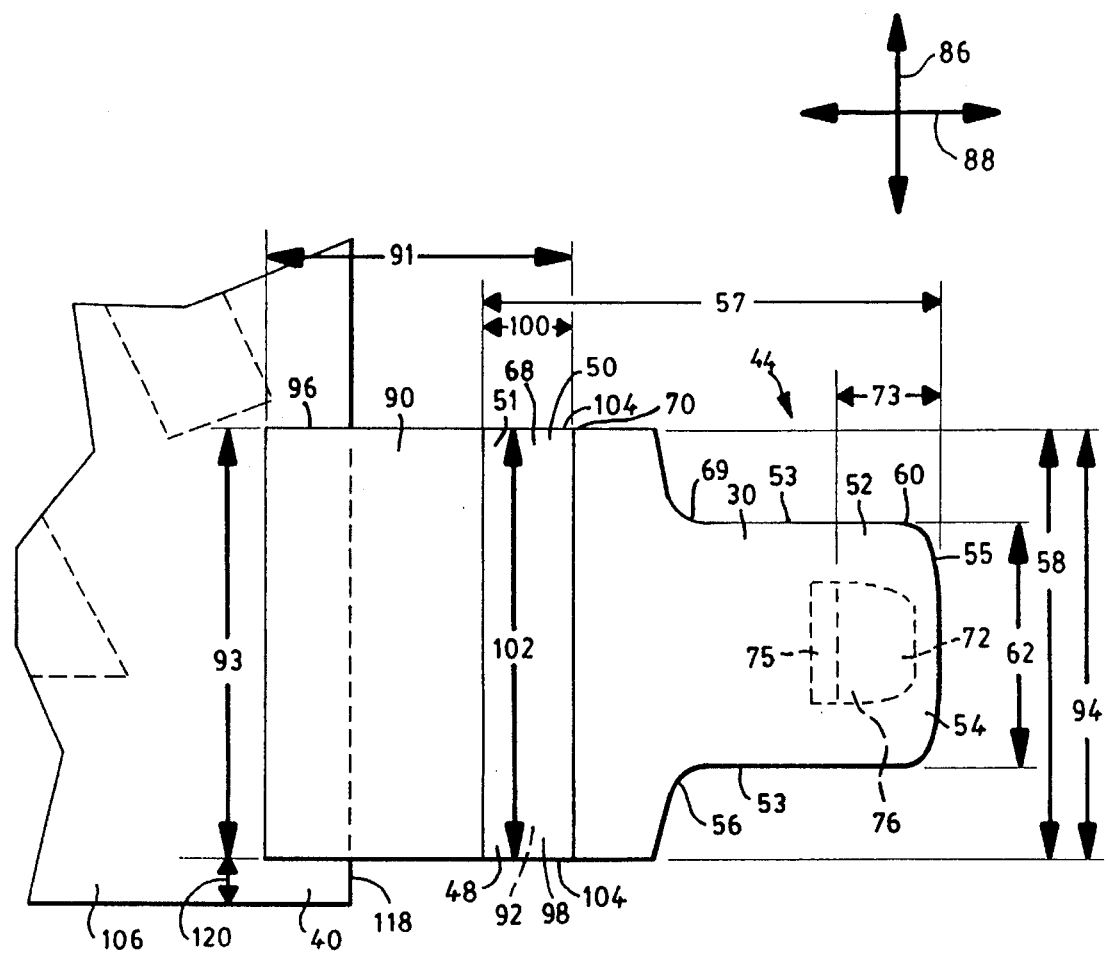
FIG. 3 representatively shows a plan view of a side panel and fastening tab assembly of the invention, where the fastener tab has a generally rectangular user-bond portion and has a gripping member which intersects the fastener substrate along a generally lengthwise extending line.
Figure 3A:
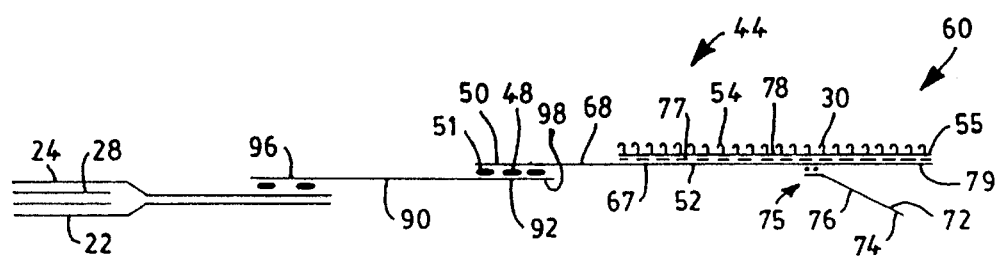
FIG. 3A representatively shows a schematic, lateral side view of the side panel and fastening tab assembly representatively shown in FIG. 3.

With reference to FIGS. 3 and 3A, the fastener tab 44 can alternatively include a generally rectangular user-bond portion 52. In addition, the stress beam length dimension can be substantially 100% of the length dimension of the side panel free end region, and the lengthwise extent of the hook material 30 can be substantially 100% of the fastener tab length 58.

Figure 4:
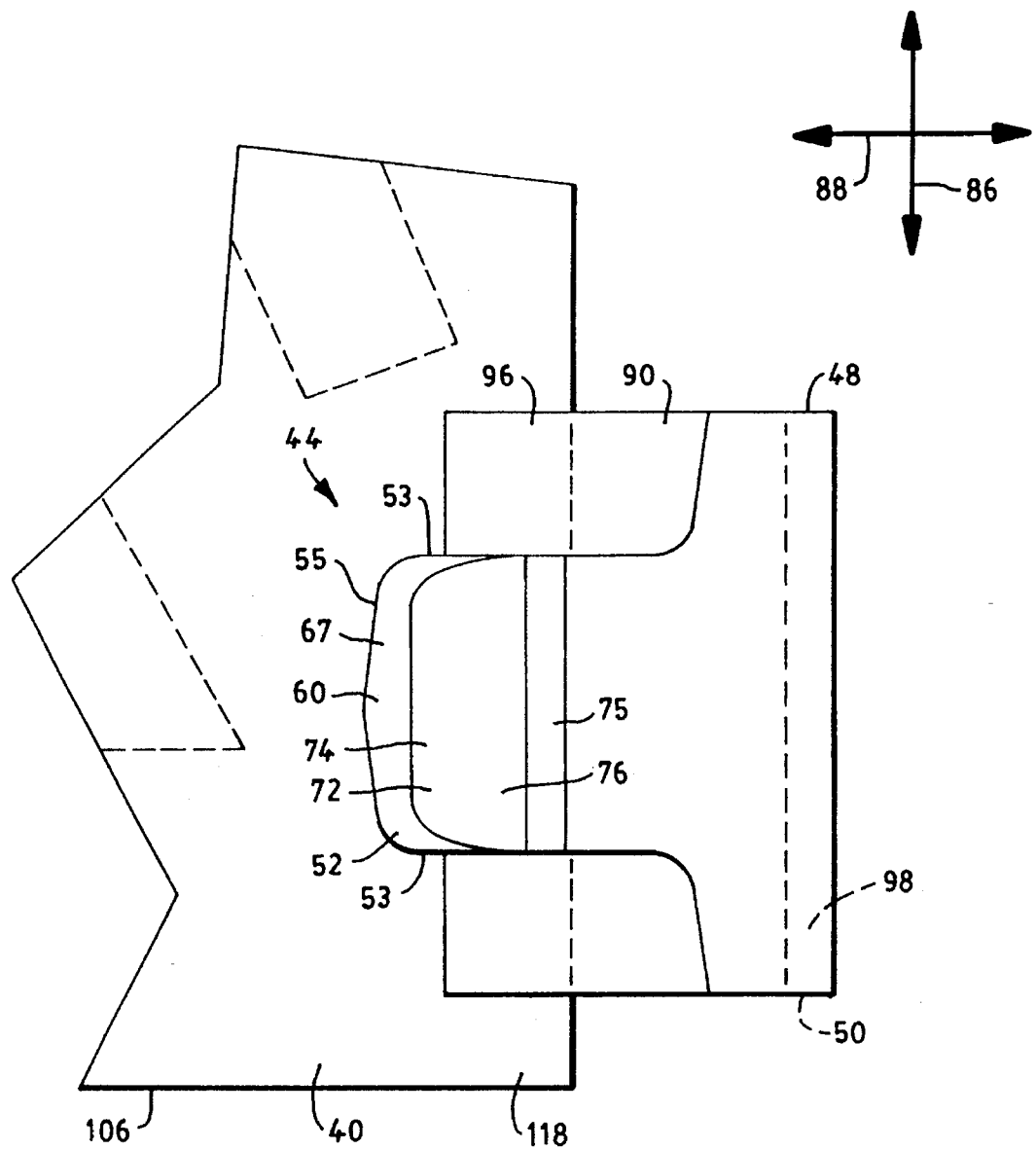
FIG. 4 representatively shows a plan view of a side panel and a folded-over fastening tab assembly in which the gripping member is provided by an L-shaped member, where a laterally extending base portion of the L-shaped member provides a laterally outboard end region of the fastener substrate.
Figure 4A:
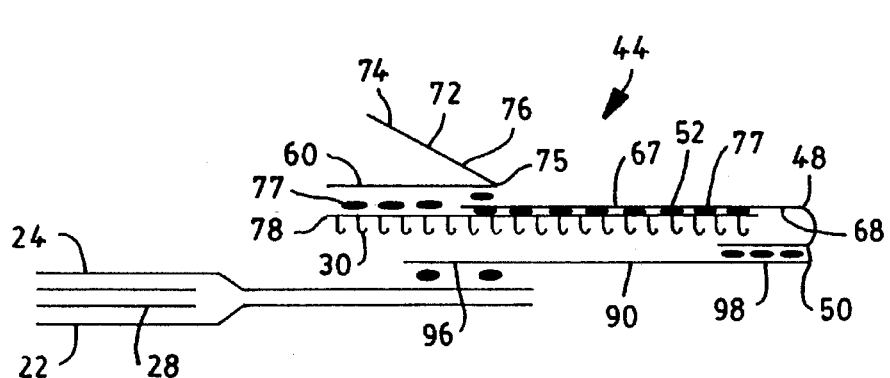
FIG. 4A representatively shows a schematic, lateral side view of the side panel and fastening tab assembly representatively shown in FIG. 4.

With reference to FIGS. 4 and 4A, the gripping member 72 can be provided by a substantially L-shaped component. The base of the "L" can be configured to provide the user-bond end section 60 of the fastener tab substrate 48, and the relatively upstanding stem of the "L" can provide the gripping member 72.

Where the user-bond end section 60 of the fastener substrate 48 is composed of a material which is different than the material of the remainder of the fastener substrate, a leading or distal region of the fastener tab 44 can be configured to have a stiffness (e.g. lower Gurley stiffness) which is lower than a stiffness of a trailing or proximal region of the fastener tab. With reference to FIGS. 4 and 4A, the appointed leading region of the fastener tab 44 is positioned between the gripping member 72 and the terminal free end of the fastener tab. The appointed trailing region of the fastener tab 44 is located between the gripping member 72 and the construction-bond portion 50 of the fastener substrate 48. The difference in stiffness values can advantageously improve the reliability of the fastening system.

With reference to FIG. 5, the fastening tab can have a generally rectangular user-bond portion and can have a gripping member 72 which intersects the fastener substrate 48 along a generally laterally extending line which extends approximately along a cross-direction of the fastener substrate. The gripping member in the shown embodiment is substantially coterminous with the fastener substrate. Optionally, the gripping member may not be coterminous with the fastener substrate and may be offset from the laterally terminal edge of the fastener substrate by a selected distance.

The securing means 54 cooperatively employed with the various configurations of the fastener substrate 48 can be provided by any operable mechanism, such as an adhesive securement bond, a cohesive securement bond, an inter-engaging mechanical securement or the like, as well as combinations thereof. For example, suitable adhesive securements can be provided by a pressure-sensitive adhesive. More particularly, the user-bond section 52 of fastening tab 44 can include a layer of primary adhesive disposed across the appointed fastening surface 68 of fastening tab substrate 48. The adhesive is configured to provide a desired level of adhesion and securement when applied against the appointed landing zone region of the article. In addition, the adhesive can be configured to be capable of being removed and refastened one or more times onto the appointed landing zone region. An example of a suitable refastenable taping system is described in U.S. Pat. No. 5,147,347, issued Sep. 15, 1992 to Y. Huang et al., the entire disclosure of which is hereby incorporated by reference in a manner that is consistent herewith.

In various alternative configurations of the invention, the fastening means may be provided by interlocking, mechanical-type fasteners such as hooks, buckles, snaps, buttons and the like. In particular aspects of the invention, the fastening means can be provided by a hook-and-loop fastener system, a mushroom-and-loop fastener system or the like (hereinafter collectively referred to as a hook-and-loop fastener). Such fastening systems generally comprise a "hook" or hook-like component, and a cooperating "loop" component which engages and interlocks with the hook component. Conventional systems are, for example, available under the VELCRO® trademark. Other examples of suitable hook-and-loop fastening systems are described in U.S. Pat. No. 5,019,073, issued May 28, 1991 to T. Roessler et al., the entire disclosure of which is hereby incorporated by reference in a manner that is consistent herewith. In a typical configuration of a hook-and-loop fastening system, a portion of hook material 30 is operably connected to the fastening surface 68 of fastening tab substrate 48, and the loop material is employed to construct at least one cooperating landing zone patch 46. The landing zone patch, for example, can be suitably attached to the appointed landing zone region on the outside surface of backsheet 22. An alternative configuration of a suitable hook-and-loop fastening system may have the loop material secured to the fastening surface 68 of fastening tab substrate 48. Accordingly, a region of hook material would be employed to form the landing zone patch 46.

In particular aspects of the invention, the hook material 30 can be of the type referred to micro-hook material. A suitable micro-hook material is distributed under the designation CS200 and is available from 3M Company, a business having offices in St. Paul, Minn. The micro-hook material can have hooks in the shape of mushroom "caps", and can be configured with a hook density of about 1600 hooks per square inch; a hook height which is within the range of about 0.013 to 0.038 inch; and a cap width which is within the range of about 0.01 to 0.013 inch. The hooks are attached to a base film substrate having a thickness of about 0.003–0.004 inch and a Gurley stiffness of about 15 mg.

In the various configurations of the invention, the loop material can be provided by a nonwoven, woven or knit fabric. For example, a suitable woven fabric can be composed of a 2 bar, warp knit fabric of the type available from Guilford Mills, Inc., Greensborough, N.C. under the trade designation #34285.

In particular aspects of the invention, the loop material need not be limited to a restricted landing zone patch 46. Instead the loop material can be provided by a substantially continuous, outer fibrous layer which is an integrated component of a cloth-like outer cover employed with the diaper 20. For example, a cloth-like backsheet 22 can be composed of the stretch thermal laminate, outer cover material previously described herein.

The securing means 54 in the various constructions of the invention can be operably attached to fastener substrate 48 by employing any one or more of the attachment mechanisms employed to construct and hold together the various other components of the article of the invention. A laterally terminal edge 55 of the attachment, which connects between securing means 54 and fastener substrate 48, is desirably positioned laterally outboard from the intersection 75 between gripping member 72 and fastener substrate 48.

The strength of the attachment interconnecting fastener substrate and securing means 54 should be greater than the peak force required to remove the fastener tab 44 from its releasable securement to the appointed attachment section of the article. Similarly, the strength of connection between gripping member 72 and fastener substrate 48 should be greater than the force required to remove the fastening tab 44 from its releasable securement to the appointed attachment section of the article.

With reference to FIGS. 2 and 2A, for example, the securing means 54 can be provided for by the representatively shown component of hook material. The hook material can include a securement substrate 78 which operably connects to the fastener substrate 48 with a suitable substrate attachment 77. The substrate attachment can be provided by any suitable construction attachment, such as adhesive bonds, thermal bonds, sonic bonds, stapling, pinning, and the like. The intersection 75 between the gripping member 72 and the fastener substrate is located laterally inboard from a terminal end 79 of the substrate attachment 77 by a selected offset distance 73.

Fastening tab 44 can advantageously have a stiffness value which is different than the stiffness value of stress beam 98. As a result, fastening tab 44 can be selectively configured with a user-bond section 52 which is capable of being fastened, removed and refastened without excessively distorting or tearing the appointed landing zone region of the article. The selective tailoring of the characteristics of fastening tab 44 can be accomplished while retaining the desired stress beam characteristics of stress beam section 98. The stress beam section can retain its ability to spread forces across the free end length 94 of side panel 90 without adversely affecting the fastening and refastening capability of fastening tab 44.

In particular aspects of the invention, the fastening tab 44 includes a substrate material which provides for a Gurley stiffness value of not more than about 3000 mg. Alternatively, the fastening tabs can be provided with a stiffness value of not more than about 1000 mg, and optionally can be provided with a stiffness value of not more than about 500 mg. In further aspects of the invention, fastener substrate provides for a Gurley stiffness value of not less than about 5 mg. Alternatively, the fastener substrate provides for a stiffness value of not less than about 10 mg, and optionally provides for a stiffness value of not less than about 25 mg. In the various configurations of the invention the desired Gurley stiffness value can be exhibited with respect to the width dimension, or with respect to both the width and length dimensions of the fastening tab.

For the purposes of the present invention, the various rigidity stiffness values are determined with respect to a bending moment produced by a force which is directed perpendicular to the plane substantially defined by the length and width of the component being tested. A suitable technique for determining the rigidity, stiffness values described herein is a Gurley Stiffness test, a description of which is set forth in TAPPI Standard Test T 543 pm-84 (Stiffness of paper (Gurley type stiffness tester)). A suitable testing apparatus is a Gurley Digital Stiffness Tester: Model 4171-D manufactured by Teledyne Gurley (514 Fulton Street, Troy, N.Y. 12181-0088). This instrument allows the testing of a wide variety of materials through the use of various lengths and widths in combination with the use of a 5, 25, 50, or 200 gram weight placed in one of three positions on the pointer of the apparatus. For purposes of the present description, the stated Gurley stiffness values are intended to correspond to the values that would be generated by a "standard" sized sample. Accordingly, the scale readings from the Gurley stiffness tester are appropriately converted to the stiffness of a standard size sample and are expressed in terms of milligrams. The standard size sample has a width of 1" and a nominal length of 3" (actual length of 3.5"). The actual length of the sample is the nominal length, plus an additional 0.25" of length for holding in the clamp and another 0.25" of length for overlapping the vane. Tables of factors for taking scale readings generated with non-standard sized test samples and converting the readings to the stiffness of the standard size sample are given in the Instruction Manual for the Gurley Stiffness Tester provided by Teledyne Gurley. Accordingly, other designated dimensions for the test sample may also be conveniently employed, so long as the appropriate conversion factor is employed to determine the appropriate value which corresponds to the standard size sample.

In particular aspects of the invention, the user-bond end section 60 of fastening tab 44 can have an end length 62 which is greater than the length 66 of the intermediate section 64 of the fastening tab, as representatively shown in FIG. 2. In the illustrated embodiment, for example, the end length can correspond to the widest length dimension of the user-bond section 52 of the fastening tab. In other aspects of the invention, the length 62 of end section 60 can also be greater than the length 58 of base section 56 of the fastening tab.

In the illustrated embodiment, for example, intermediate section 64 of fastener tab 44 can be configured to provide an expanding area of the fastener tab. The expanding area provides a gradual transition between base length 58 and end length 62. To avoid the generation of excessive stress concentrations that might initiate undesired fractures, the transition area is substantially free of sharp notches or abrupt angles.

The relatively intermediate lengths of tab 44 can advantageously contribute to the improved performance provided by the invention. The relatively larger length at the end portion of the user-bond section 52 helps provide for a larger user-bonding area which can improve the security of the fastening system. At the same time, the relatively smaller length at the intermediate portions of tab 44 can provide for a relatively greater ease of bending and/or twisting or other movement, as compared to the user-bond portion of the tab. As a result, the fastening securement can be maintained at high levels while allowing substantially continual, dynamic fit adjustments at the points of interconnection between the front and rear waistband sections of the article.

With reference to FIGS. 2 and 3, a tape fastener tab 44 can comprise a tape substrate member 48 having the desired fastening means, such as primary adhesive layer or hook material 30, located and disposed on a major facing surface of the fastener tab, such as surface 68. The substrate member can, for example, be composed of a fabric material or a suitable polymer film material, such as polypropylene, polyethylene or other suitable polyolefin. The material comprising substrate member 48 may be opaque, translucent or transparent, as desired, and may include graphics thereon. Optionally, the material may be tinted and/or textured, and may also be selectively embossed. In particular aspects of the invention, substrate member 48 can be constructed of a substantially non-extensible and/or substantially non-elastomeric material to provide desired benefits.

The fastener tab provides a construction-bond section 50 for connecting the tape substrate member to a selected portion of diaper 20, and a user-bond section 52 for connecting and securing the waistband sections of the diaper about the body of a wearer. In the illustrated configuration of the invention, the construction-bond section of fastener tab 44 is attached to the free end region 92 of side panel 90, and is constructed and configured to provide stress beam section 98. User-bond section 52 can be operably connected to a conventional finger tab which includes a substantially non-securing grasping section thereof.

The construction-bond region 50 of tape fastener 44 is generally appointed for securement onto the desired section of its associated article during the manufacture of the article. The user-bond region 52 of tape fastener 44 is appointed for securing the article on a wearer during use. The representatively shown embodiment of the tape fastener, for example, has hook material 30 applied onto a selected surface thereof to provide a mechanical fastening system. In the illustrated embodiment of diaper 20, the construction-bond region 50 of tape fastener 44 is attached to the lateral ends of the rear waistband 40, and the user-bond region 52 of the tape fastener is employed to attach the lateral ends of rear waistband 40 to the corresponding lateral ends of front waistband 38 to secure the diaper about the waist of a child. The user-bond section 52 connects to the gripping member 72, and an appointed grasping section of the gripping member can comprise a layer of exposed absorbent material, such as an absorbent nonwoven fabric. At least a portion of the exposed absorbent material can be operably positioned and arranged to face in the same direction as an appointed inward face of the tape fastener. In desired arrangements, the absorbent material is capable of absorbing oils and lotions. Examples of suitable finger tab constructions are described in U.S. Pat. No. 5,288,546, issued Feb. 22, 1994 to T. Roessler et al., the entire disclosure of which is incorporated by reference in a manner that is consistent herewith.

With an adhesive fastening tab, the securing means 54 can include a primary adhesive layer disposed upon an appointed inwardly facing surface of substrate member 48. The portion of the adhesive positioned on the construction-bond 50 can be employed to assemble tape fastener 44 onto diaper 20 during the manufacture of the diaper. The portion of adhesive layer located on user-bond region 52 can be employed to secure the diaper onto an infant. The particular adhesive parameters of the adhesive layer can be selected and tailored to meet desired adhesive properties, such as adhesive shear strength and adhesive peel strength. Examples of suitable adhesive tab configurations are described in U.S. patent application Ser. No. 08/168,615 of T. Roessler et al., entitled DYNAMIC FITTING DIAPER and filed Dec. 16, 1993.

Suitable materials for constructing fasteners 44, such as sheet materials for constructing substrate member 48 and fastening materials for constructing the securing means 54, are available from various manufacturers, such as 3M Company, a business having a Disposable Products Division with offices in the 3M Center, St. Paul, Minn.; and Avery International, a business having a Specialty Tape Division with offices in Painesville, Ohio. The user-bond region of tape substrate member 48 may have a terminal, distal end section which is appointed for grasping by the user to suitably position and adhere the user-bond region of tape fastener 44 to an appointed tape securement zone of the article. For example, the user may typically grasp the end section to attach the tape fastener against the appointed attachment landing zone on the article 20. The distal end section can be constructed to be non-adhering and non-securing so that the end section can be more easily found and lifted by the user. In a particular construction of the invention, tape fastener 44 can include a separate finger lift tab member attached to a terminal edge region of the substrate end section 60.

In desired configurations, the finger tab may be eliminated and the gripping member 72 can be operably connected to the user surface 67 of the fastener substrate 48 to provide a fastening system that is refastenable and is more resistent to "pop-opens", or other inadvertent or undesired releases of the fastener. The gripping member system can advantageously increase the amount of applied force needed to initiate the separation and release of the fastener. As a result, a securing means which might ordinarily separate under relatively low levels of peel force, such a micro-hook material, can be employed to provide a reliable fastening system.

In the various configurations of the invention, the area of the intersection 75 between gripping member 72 and fastener substrate is positioned laterally inboard from the terminal, free edge of the user-bond end section 60 by a predetermined spacing offset distance 73. More particularly, In particular aspects of the invention, the offset distance is at least about 0.2 cm. Alternatively, the offset distance is at least about 0.5 cm, and optionally is at least about 0.75 cm to provide improved benefits. In other aspects of the invention, the offset distance can be up to about 2 cm, and optionally, can be up to about 5 cm to provide desired performance attributes.

The gripping member 72 can be a separate component which is assembled and fixedly attached to the substrate user surface, as representatively shown in FIGS. 2 and 2A. Alternatively, the gripping member 72 can be integrally formed from at least a portion of the material employed to provide the fastener substrate 48, as representatively shown in FIGS. 4 and 4A.

In the various configurations of the invention, the gripping member 72 can have a variety of shapes and constructions. For example, the gripping members 72 can have a generally strip configuration which intersects the fastening substrate 48 at a location which is intermediate the side edge regions 53 of the fastener substrate 48, as representatively shown in FIGS. 9 and 9A, and by Code G of the Examples. Alternatively, the width 148 of the gripping member can be decreased to provide a string configuration which intersects the fastening substrate 48 at a location which is intermediate the side edge regions of the fastener substrate.

In other arrangements, gripping member 72 can have a flap-like, sheet configuration which intersects the fastener substrate 48 along a line which extends approximately along a length direction 86 of the fastening tab 44. In particular aspects of the invention, the gripping member 72 can be positioned into a substantially parallel, adjacent relation with the user surface 67 of the fastener substrate 48. In other aspects of the invention, the distal end portion 74 of the gripping member 72 can be constructed to extend beyond the terminal edge of the user-bond end section 60 by a selected distance when the gripping member is positioned into the substantially parallel, adjacent relationship. Optionally, the distal end of the gripping member can extend a distance which stops short of or is equal to the location of the terminal edge of the user-bond end section 60 of the fastener substrate.

Where gripping member 72 intersects fastener substrate 48 along a line which extends approximately along a longitudinal direction 86 of the fastener substrate, the length of the line exhibited by intersection 75 can be less than the entire lengthwise extent of the fastener substrate 48. Accordingly, each of the side edges of the gripping member is spaced away from its correspondingly adjacent side edge 53 of the fastener substrate 48 by a predetermined inset distance.

An alternative configuration of gripping member 72 can include a flap-like sheet component which intersects the fastener substrate 48 along a line which extends approximately along a lateral width dimension 88 of the fastening tab 44, as representatively shown in FIG. 5. With this arrangement, the entirety of the area of the intersection 75 between gripping member 72 and fastener substrate is positioned laterally inboard from the terminal edge of the user-bond end section 60. In addition, the line of intersection between gripping member 72 and fastener substrate 48 can be substantially entirely located between the side edges 53 of the fastener substrate 48.

The gripping member can be composed of various suitable materials. Examples of such materials include films, nonwoven fabrics, woven or knit fabrics and foams, as well as laminates and composites thereof. In addition, the gripping member can be include an elastomeric material to elasticize the gripping member.

Figure 6:
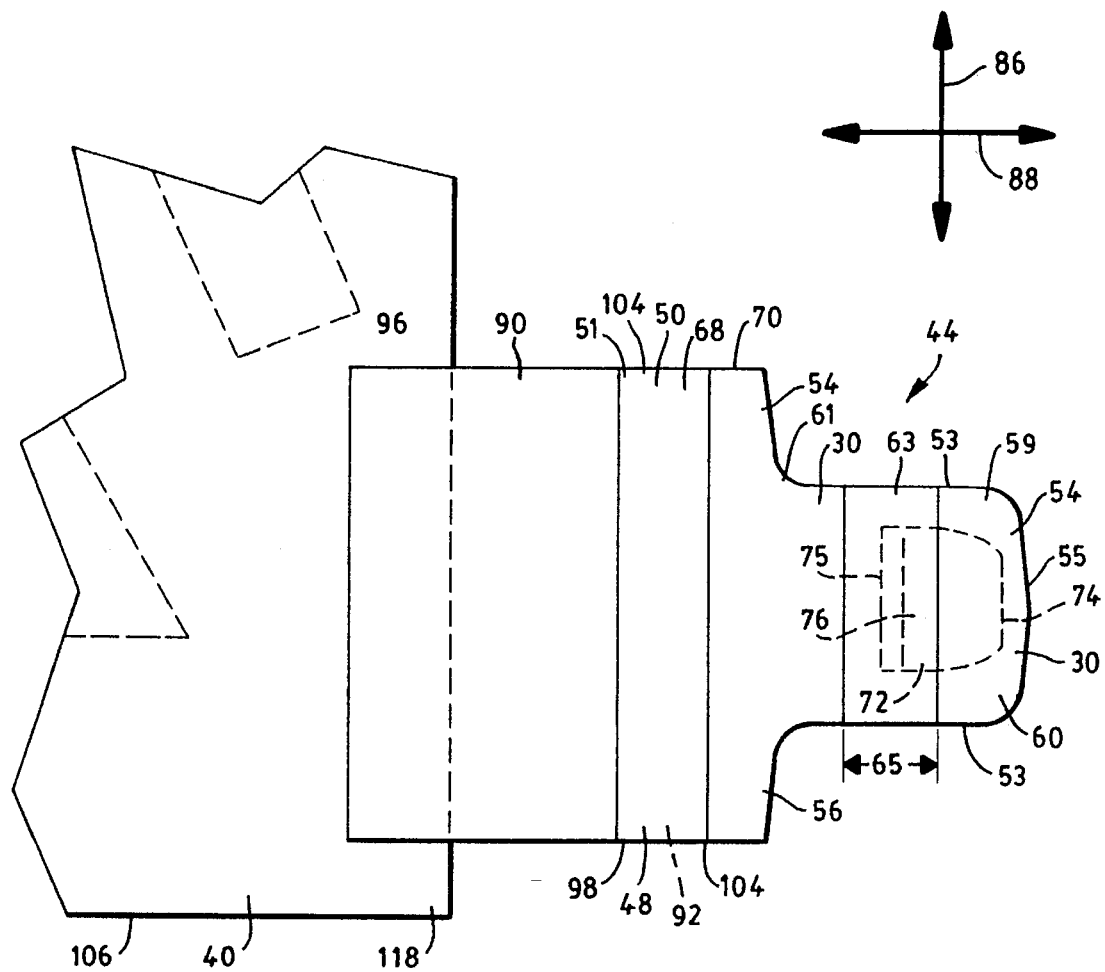
FIG. 6 representatively shows top plan view of a side panel and fastening tab assembly in which the hook material has a leading section and a trailing section which is spatially separated from the leading section by a discrete lateral distance.
Figure 6A:
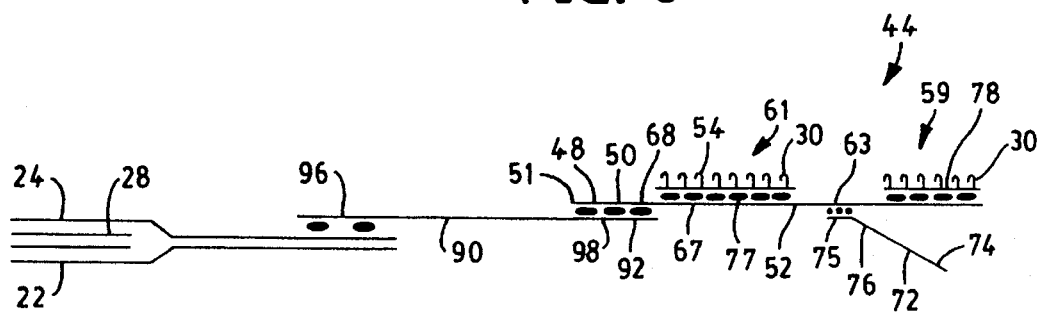
FIG. 6A representatively shows a schematic side view of the fastening tab assembly illustrated in FIG. 6.

With reference to FIGS. 6 and 6A, the securing means, such as provided by the illustrated hook material 30, can include an appointed leading region 59 which is positioned outboard toward the user-bond end section 60, and an appointed trailing region 61 which is relatively positioned inboard toward the construction-bond portion 50 of the fastener substrate 48. Gripping member 72 can advantageously be configured to intersect the fastener substrate 48 at a location which is substantially intermediate the appointed leading region 59 and trailing region 61 of the selected securing means.

In particular aspects of the invention, the leading region 59 of the securing means can be spatially separated from the trailing region 61 of the securing means by a selected spacing distance 65 which provides for a spacing region 63 which is substantially free of the securing means and has a non-securing construction. In other configurations of the invention, the leading region 59 of the securing means can be substantially coterminous with a laterally terminal, distal edge region of the fastener substrate 48.

In further aspects of the invention, the separation distance between the leading region 59 and the trailing region 61 of the securing means is not less than about 0.2 cm. Alternatively, the spacing distance is not less than about 0.5 cm, and optionally is not less than about 0.75 cm. In other aspects of the invention, the separation distance between the leading region and trailing region of the securing means is not more than about 10 cm. Alternatively, the spacing distance is not more than about 8 cm, and optionally, is not more than about 5 cm to provide desired performance.

In further aspects of the invention, the fastening system may incorporate the primary stress beam section 98 and at least another optional, supplemental beam section. The supplemental beam section may be substantially coterminous with its associated waistband end section 116 or 118, or may be spaced away from the terminal edge of the associated waistband end sections by a selected discrete distance.

In the illustrated configurations a waistband section, such as rear waistband section 40 of the article, has at least one lateral end region 118 to which is attached a side panel 90. Typically, the article has another oppositely located waistband end region which has a similar, mirror-image configuration and construction. End region 118 can optionally include a supplemental stress beam section which extends along the length dimension of the waistband end region and also has a selected width dimension. The construction of the supplemental stress beam section can incorporate the various structures and configurations described with regard to the primary stress beam section 98.

When employing the supplemental stress beam, the supplemental beam is able to accept the force imparted through side panel 90 and distribute the force over a wider area of the chassis structure of the diaper. This can help avoid undesirable stress concentrations that might tear or excessively deform localized areas of the diaper components.

The fastener system of the present invention can have improved resistance to undesired pop-opens. In particular, the fastener system can increase the removal force needed to peel the fastener tab away from its securement to the appointed fastening attachment section of the article. A suitable technique for determining the force required to remove a fastener off of its appointed attachment substrate can be determined by a modified Pressure Sensitive Tape Council Test Procedure PSTC-1 (Peel Adhesion for Single Coated Pressure Sensitive Tapes at 180° Angle), which is described in the following Peel Test Procedure.

PEEL TEST PROCEDURE

With reference to FIGS. 7 and 7A, a steel test plate 124 and a test substrate 126 each have a width dimension 132 of 2 inches and a length dimension 134 of 5 inches. Double-sided adhesive tape 128 (1 inch wide) is applied to the opposed, length-wise ends of the stainless steel panel plate. The bonding attachment strength of the tape should be greater than the forces generated during the test. An example of a suitable double-sided tape is a clear transfer tape #465 available from 3M Company. Sufficient double-sided tape is employed to extend completely across the 2 inch width of the steel test panel. The test substrate 126 is composed of the appointed landing attachment zone material, and is secured to the test plate with the double-sided tape.

The fastener test sample 140 includes an area of securement material which has a width dimension 142 of 1 inch and a length dimension 144 of 2 inches. The gripping member tab 72 has a length 146 of 1 inch, and has a width 148 (FIGS. 8 and 9) which is selected in accordance with the desired fastener design. Approximately 0.25 inch of one end of the gripping tab is adhered to a leading strip 130 using double-sided adhesive tape. The leading strip 130 is a non-stretchable material, such as Kraft wrapping paper, and should be stronger than the peak removal force generated during the testing. The leading strip has the same width 136 as the gripping tab 72 and has a strip length 138 of 8 inches. The fastener test sample 140 is pressed down to the center of the test substrate 126 with a standard 4.5 lb mechanical roller (available from Chemsultants International located in Mentor, Ohio) by rolling the roller across the fastener test sample once in each direction. The 180° peel adhesion test is then conducted immediately thereafter.

When placing the test specimen in the peel tester, the jaws of the selected tensile tester are initially set at 8 inches apart. A one inch length of a base end 122 of the steel test plate is secured in the stationary jaw with the unsecured leading strip 130 extending past the position of the stationary jaw. The leading strip is then doubled-back, and clamped in a centered arrangement within the moving jaw of the tester. The tester is then activated to conduct the 180° peel at a speed of 300 mm/min. The moving jaw travels a total distance about 70 mm. The peel force in terms of grams is recorded as a function of peel distance. The recording can be performed by a chart recorder or a computer. The peak removal force is the highest force shown on the curve generated by plotting the peel force as a function of the peel distance.

The following Examples are provided to give a more detailed understanding of the invention. The particular amounts, proportions, compositions and parameters are meant to be exemplary, and are not intended to specifically limit the scope of the invention.

EXAMPLES 1–5

Figure 8:
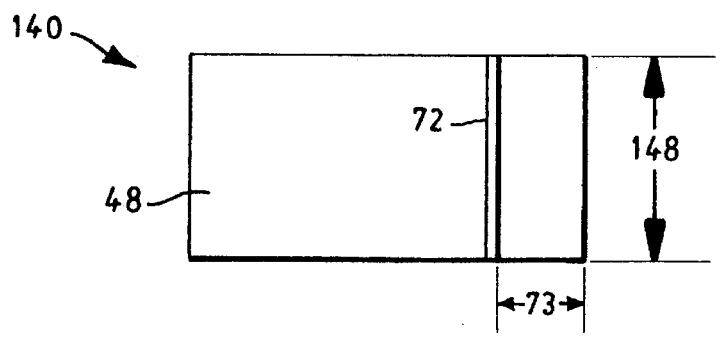
FIG. 8 representatively shows a top plan view of a fastener tab sample having a gripping member which is offset from a terminal end of the securing means of the fastener tab.
Figure 8A:
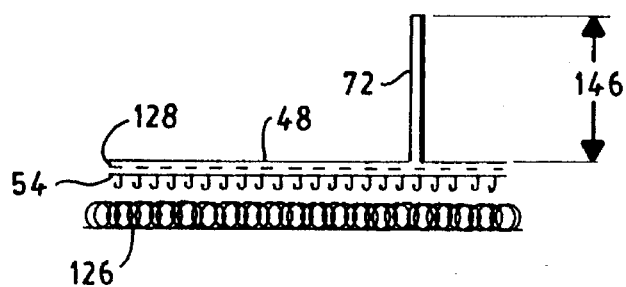
FIG. 8A representatively shows a schematic side view of the fastener tab sample of FIG. 8.

With reference to FIGS. 8 and 8A, five test samples designated Code A were each constructed with a fastener substrate 48 composed of 1.7 ounce per square yard (57.8 gsm), spunbond-meltblown-spunbond (SMS) nonwoven fabric in which the component layers were bonded together with sufficient strength to withstand the testing without delamination or tearing. The SMS fabric included a 15.3 gsm polypropylene meltblown layer sandwiched between two, 21.25 gsm, polypropylene spunbond outer layers.

The securing means 54 of each test sample included a CS200 micro-hook material obtained from 3M Company, St. Paul, Minn. which was permanently affixed to the appointed fastening surface of the substrate 48 with double-sided tape. The securing means also included a cooperating loop material which was employed to construct test substrate 126. Accordingly, the loop material was affixed to test plate 124 (FIG. 7). The loop material was composed of a stretch thermal laminate (STL) material composed of a 0.6 mil (0.015 mm) thick polypropylene blown film and a 0.7 ounce per square yard (23.8 gsm) polypropylene spunbond material (2 denier fibers). A material of this type forms the outercover of the HUGGIES® Supreme diaper, which is commercially available from Kimberly-Clark Corporation.

The gripping member 72 had a width 148 of 1 inch, which equaled the width of the test sample, and had an offset distance 73 of zero inches. In addition, the gripping member was composed of a double layer of the material employed to form substrate 48, as shown.

The Code A samples were tested with the above-described Peel Test procedure, and the results are set forth in the table of FIG. 11.

EXAMPLES 6–10

Five test samples designated Code B were prepared. The construction of the Code B samples was the same as the construction of the Code A samples, except that the gripping member 72 had an offset distance 73 of 0.25 in. The Code B samples were tested with the above-described Peel Test procedure, and the results are set forth in the table of FIG. 11.

EXAMPLES 11–15

Five test samples designated Code C were prepared. The construction of the Code C samples was the same as the construction of the Code A samples, except that the gripping member 72 had an offset distance 73 of 0.5 in. The Gurley stiffness of the fastener substrate was about 149 mg. The Code C samples were tested with the above-described Peel Test procedure, and the results are set forth in the table of FIG. 11.

EXAMPLES 16–20

Five test samples designated Code D were prepared. The construction of the Code D samples was the same as the construction of the Code A samples, except that the gripping member 72 had an offset distance 73 of 0.75 in. The Code D samples were tested with the above-described Peel Test procedure, and the results are set forth in the table of FIG. 11.

EXAMPLES 21–25

Figure 9:
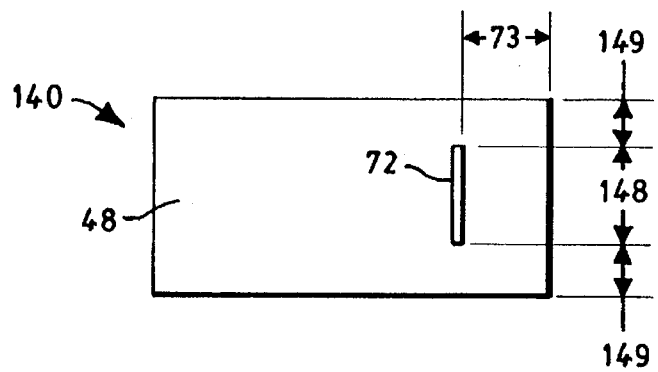
FIG. 9 representatively shows a top plan view of a fastener tab sample having a gripping member which is offset from a terminal end of the securing means of the fastener tab and is inset from the laterally extending side edges of the fastener tab.
Figure 9A:
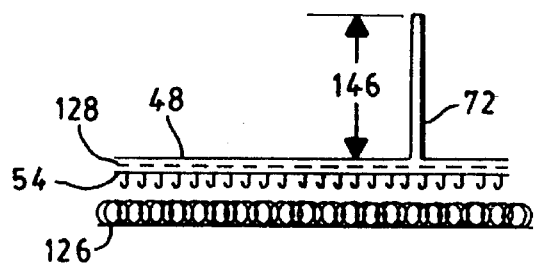
FIG. 9A representatively shows a schematic side view of the fastener tab sample of FIG. 9.

With reference to FIGS. 9 and 9A, five test samples designated Code E were prepared. The construction of the Code E samples was the same as the construction of the Code C samples, except that the gripping member 72 had an additional inset distance 149 which measured 0.125 inch from each side edge of the test sample. The Code E samples were tested with the above-described Peel Test procedure, and the results are set forth in the table of FIG. 12.

EXAMPLES 26–30

Five test samples designated Code F were prepared. The construction of the Code F samples was the same as the construction of the Code C samples, except that the gripping member 72 had an inset distance 149 from each side edge of the test sample, which measured 0.25 in. The Code F samples were tested with the above-described Peel Test procedure, and the results are set forth in the table of FIG. 12.

EXAMPLES 31–35

Five test samples designated Code G were prepared. The construction of the Code G samples was the same as the construction of the Code C samples, except that the gripping member 72 had an inset distance 149 from each side edge of the test sample, which measured 0.375 in. The Code G samples were tested with the above-described Peel Test procedure, and the results are set forth in the table of FIG. 12.

EXAMPLES 36–40

Figure 13:
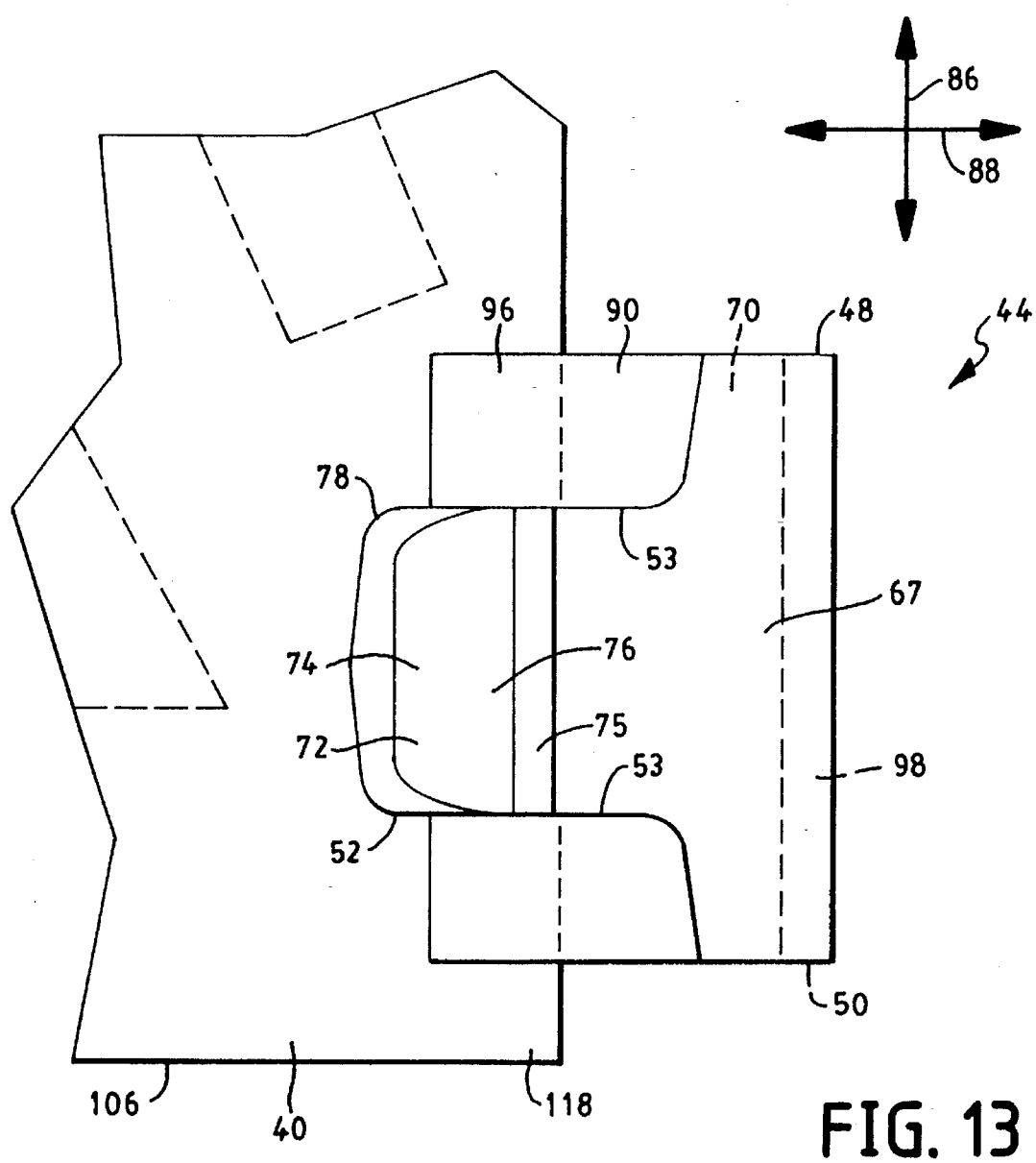
FIG. 13 representatively shows a top plan view of a side panel and fastening tab assembly in which a securement and support substrate of the hook material extends beyond a terminal edge of the fastener substrate.
Figure 13A:
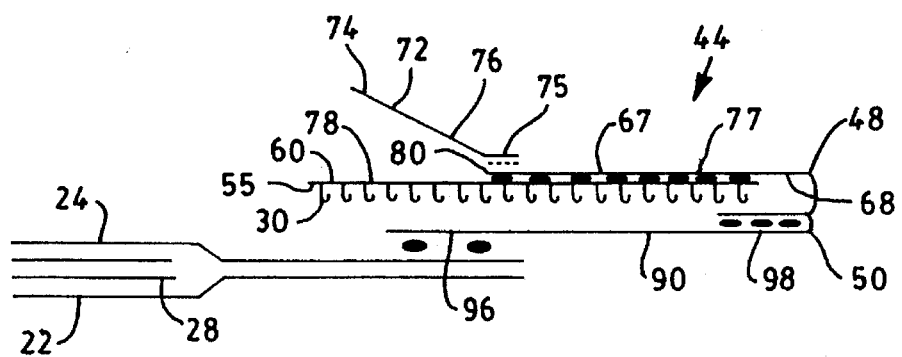
FIG. 13A representatively shows a schematic side view of the fastening tab assembly illustrated in FIG. 13.

With reference to FIGS. 13 and 13A, five test samples designated Code H were prepared. The construction of the Code H samples was the same as the construction of the Code C samples, except that the fastener substrate 48 had a length of 1.5 inch, and the securement substrate 78 of hook material 30 extended past the terminal edge 80 of the fastener substrate 48 by a distance of 0.5 inch. The Gurley stiffness of the distal end section of the hook material, which extended past the terminal edge 80 of the fastener substrate 48, was about 15.4 mg. The gripping member 72 intersected the fastener substrate at substantially the terminal edge of the fastener substrate, and was integrally formed as an extension of the material layer that provided the fastener substrate 48. Alternatively, the gripping member can be a separate component which is joined and affixed to the fastener substrate, as illustrated in FIG. 13A. The Code H samples were tested with the above-described Peel Test procedure, and the results are set forth in the table of FIG. 14. In test samples 3 and 5 of Code H, the samples failed when the fastener substrate 48 delaminated from the securement substrate 78.

EXAMPLES 41–45

Figure 10:
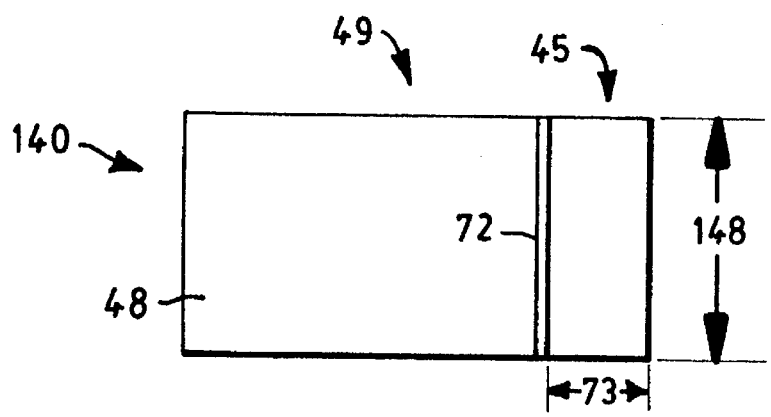
FIG. 10 representatively shows a top plan view of a fastener tab sample having a gripping member which is offset from a terminal end of the securing means of the fastener tab and wherein the fastener substrate has distal and proximal sections composed of materials having different stiffness.
Figure 10A:
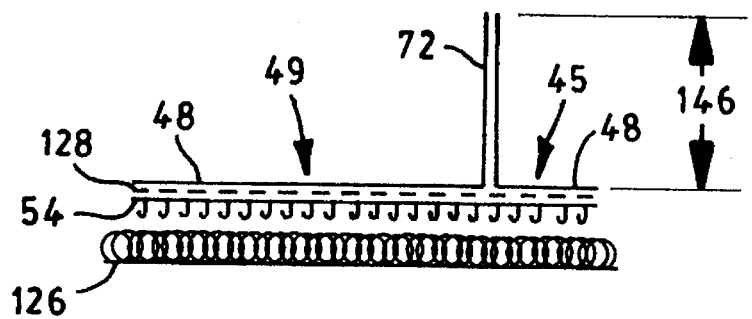
FIG. 10A representatively shows a schematic side view of the fastener tab sample of FIG. 10.

With reference to FIGS. 10 and 10A, five test samples of a fastening tab designated Code J were each constructed with a multi-component fastener substrate 48. As a result, the fastening tab sample 140 had a proximal section 49 and a distal section 45. The proximal section of the fastener substrate 48 was composed of a 1.7 ounce per square yard (57.8 gsm) spunbond-meltblown-spunbond (SMS) non-woven fabric in which the component layers were bonded together with sufficient strength to withstand the testing without delamination or tearing. The SMS fabric included a 15.3 gsm polypropylene meltblown layer sandwiched between two, 21.25 gsm, polypropylene spunbond outer layers. The distal section of the fastener substrate was composed of a 0.7 ounce per square yard (21.7 gsm) spunbond nonwoven fabric, and the intermediate, extending flap portions of the distal and proximal sections of the fastener substrate materials were laminated together to form the gripping member 72. The securing means 54 of each test sample included a CS200 micro-hook material obtained from 3M Company, which was permanently affixed to the appointed fastening surfaces of the distal and proximal sections of the fastener substrate 48. The overall composite at the distal section of the fastener tab sample had a Gurley stiffness of about 45 mg.

The gripping member 72 had a width 148 of 1 inch, which equaled the width of the test sample, and had an offset distance 73 of 0.5 inches. The Code J samples were tested with the above-described Peel Test procedure, and the results are set forth in the table of FIG. 14. The Code J samples indicate that constructing the fastener substrate with a relatively low stiffness distal section 45 which extends to a location that is at least coterminous with the securing means can advantageously prevent undesired delaminations of the fastener structure.

Figure 15:
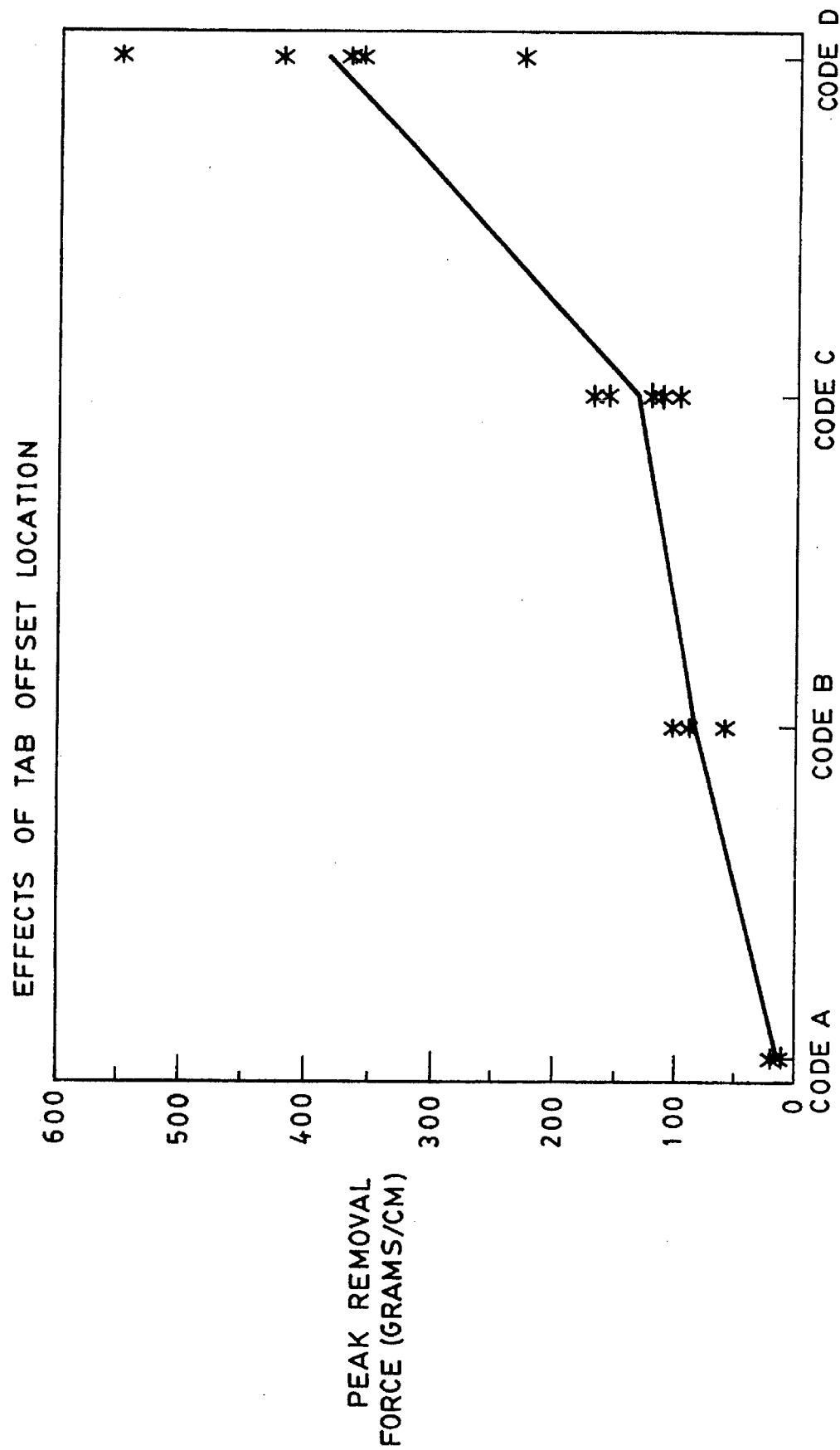
FIG. 15 shows a graph of the data regarding the effects of the offset location of the gripping member.

With reference to the graph of FIG. 15, it was found that, as the offset distance 73 increased from zero inches (Code A) to 0.75 inches (Code D), the peak removal force increased from about 14 grams/cm to about 386 gm/cm. This graph illustrates the significant effects of tab offset location on the peak removal force, and shows that one can tailor the peak removal force of a fastening system by selecting a desired offset location.

Figure 16:
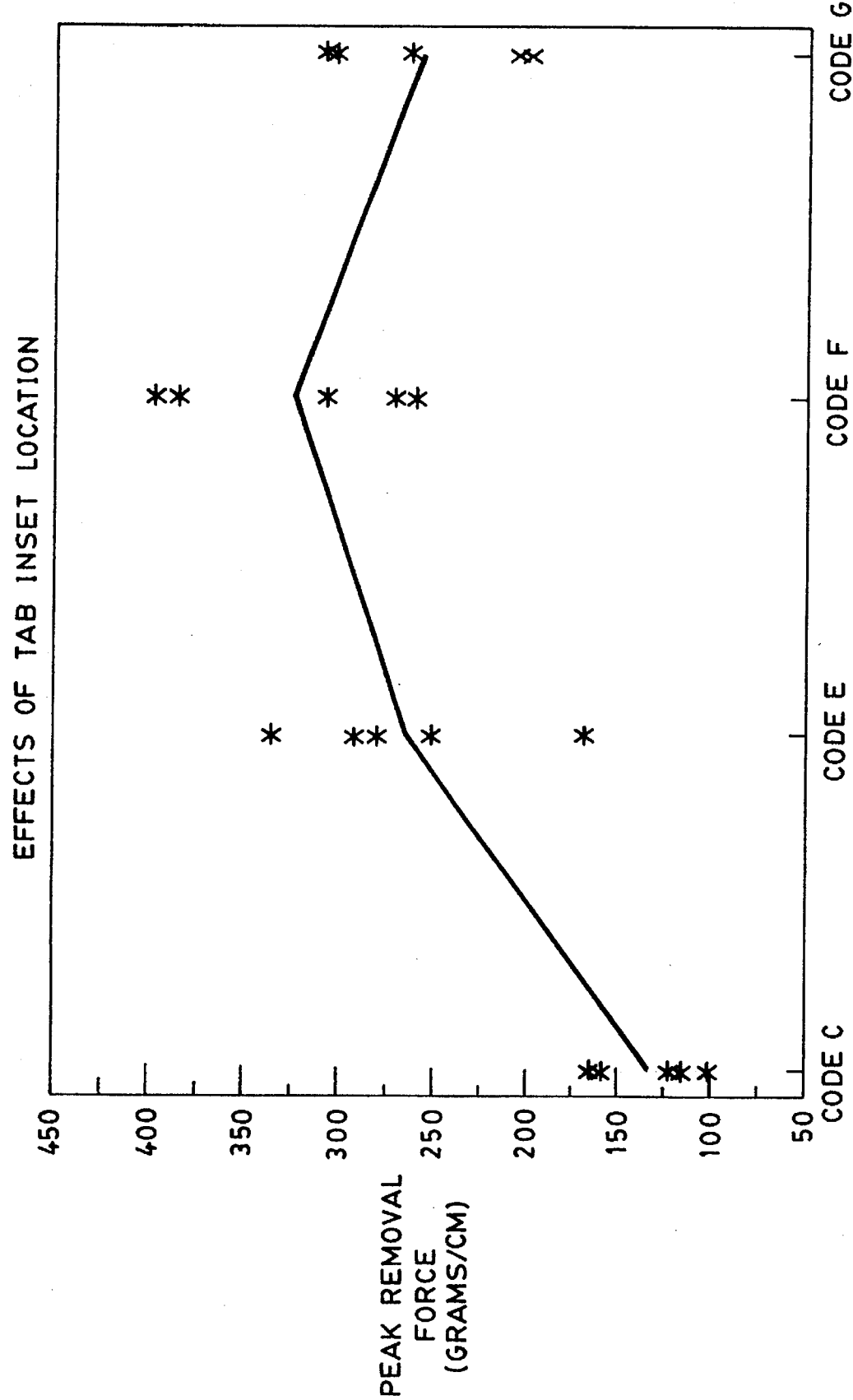
FIG. 16 shows a graph of the data regarding the effects of the inset location of the gripping member.

With reference to the graph of FIG. 16, it was found that, with a single selected offset distance (such as a distance of 0.5 inch), the peak removal force of the fastener system increased from about 133 grams/cm to about 324 gram/cm when the inset distance 149 increased from zero inches (Code C) to 0.25 inch (Code F). The peak removal force decreased slightly when the inset distance 149 was further increased from 0.25 inch (Code F) to 0.375 inch (Code G). This indicates that within a certain range of distances, the peak removal force increases with increasing inset distance. When the inset distance exceeds a certain amount, the gripping member 72 can becomes very narrow. As a result, the force applied to the gripping member can become concentrated around the gripping member, and the peak force required to separate the fastener tab from the substrate can decrease. Thus, the graph illustrates how the peak removal force can advantageously be adjusted by changing the inset distance 149.

With reference to the graph of FIG. 17, it was found that, as the Gurley stiffness of the leading, distal section of the fastener tab decreased from about 149 mg (Code C) to about 15.4 mg (Code H), the peak removal force increased from about 133 gram/cm to about 66 gram/cm. The graph shows that an increase in the flexibility of leading region of the fastening tab structure can increase the peak removal force of the fastening system. It was also found that the high peak removal forces can cause undesired delamination of the securing means from the fastener substrate unless additional structures are provided to reinforce the attachment between the securing means and the fastener substrate or to reduce the stress concentrations that may cause the delamination.

Having thus described the invention in rather full detail, it will be readily apparent that various changes and modifications can be made without departing from the spirit of the invention. All of such changes and modifications are contemplated as being within the scope of the invention, as defined by the subjoined claims.

We claim:

1. A fastening tab, comprising:
   a fastener substrate having a construction-bond portion for attaching said fastener substrate to an article, a user-bond portion connected to said construction-bond portion, a user-bond end edge section, a construction-bond end edge section, a pair of opposed side edge sections, a fastening surface and a user surface;
   securing means connected to said fastening surface of said fastener substrate at least along said user-bond portion thereof for securing said user-bond portion; and
   a gripping member affixed to said user surface at said user-bond portion of said fastener substrate for applying a force for removing said securing of said user-bond portion of said fastening tab, said gripping member having a distal end portion which is substantially free and a base portion which is operably connected to the user surface of said fastener substrate, said gripping member configured to intersect said fastener substrate at said base portion at an intersect location which is spaced from said construction-bond portion, is positioned to extend between said fastener substrate side edge sections, and is positioned between said construction-bond portion and said user-bond end edge section of said fastener substrate, said intersect location positioned laterally inboard from a terminal free edge of said user-bond end section of said fastener substrate by a predetermined spacing distance.

2. A fastening tab as recited in claim 1, wherein said securing means includes a leading region positioned toward said user-bond end edge section and a trailing region positioned toward said construction-bond portion of said fastener substrate; and wherein said gripping member is configured to intersect said fastener substrate at a location which is intermediate said leading region and trailing region of said securing means.

3. A fastening tab as recited in claim 2, wherein said securing means includes means for providing an adhesive securement.

4. A fastening tab as recited in claim 2, wherein said securing means includes means for providing a cohesive securement.

5. A fastening tab as recited in claim 2, wherein said securing means includes means for providing an inter-engaging mechanical securement.

6. A fastening tab as recited in claim 5, wherein said securing means comprises a hook component of a hook-and-loop fastener.

7. A fastening tab as recited in claim 5, wherein said securing means comprises a loop component of a hook-and-loop fastener.

8. A fastening tab, comprising;
   a fastener substrate having a construction-bond portion for attaching said fastener substrate to an article, a user-bond portion connected to said construction-bond portion, a user-bond end edge section, a construction-bond end edge section, a pair of opposed side edge sections, a fastening surface and a user surface;
   securing means connected to said fastening surface or said fastener substrate at least along said user-bond portion thereof for securing said user-bond portion; and
   a gripping member affixed to said user surface at said user-bond portion of said fastener substrate for applying a force for removing said securing of said user-bond portion of said fastening tab, said gripping member having a distal end portion which is substantially free and a base portion which is operably connected to the user surface of said fastener substrate, said gripping member configured to intersect said fastener substrate at a location which is spaced from said construction-bond portion, is positioned to extend between said fastener substrate side edge sections, and is positioned between said construction-bond portion and said user-bond end edge section of said fastener substrate, said gripping member having a flap-like, sheet configuration which intersects said fastener substrate along a line which extends laterally approximately along a cross-direction of said fastener substrate.

9. A fastening tab as recited in claim 1, wherein said gripping member has a sheet configuration which intersects said fastener substrate at said base portion of the gripping member and along a line which extends approximately along a longitudinal-direction of said fastener substrate.

10. A fastening tab as recited in claim 1, wherein said gripping member has a strip configuration which intersects said fastener substrate at a location which is intermediate said side edge regions of said fastener substrate.

11. A fastening tab as recited in claim 2, wherein said leading region of said securing means is spatially separated from said trailing region of said securing means by a selected distance which is substantially non-securing.

12. A fastening tab as recited in claim 2, wherein said leading region of said securing means is substantially coterminous with a laterally terminal edge of said fastener substrate.

13. A fastening tab as recited in claim 1, wherein said securing means includes a securement substrate which connects to said fastener substrate with a substrate attachment, and wherein said intersection between said gripping member and said fastener substrate is located laterally inboard from a terminal end of said substrate attachment.

14. An article, comprising:
   a fastener section and a landing attachment section, said fastener section appointed for selectively joining to said landing attachment section; and
   at least one fastening tab for joining said fastener section to said landing attachment section, said fastening tab including;
      a fastener substrate having a construction-bond portion for attaching said fastener substrate to an article, a user-bond portion connected to said construction-bond portion, a user-bond end edge section, a construction-bond end edge section, a pair of opposed side edge sections, a fastening surface and a user surface;
      securing means connected to said fastening surface of said fastener substrate along said user-bond portion thereof for securing said user-bond portion; and
      a gripping member affixed to said user surface at said user-bond portion of said fastener substrate for applying a force for removing said securing of said user-bond portion of said fastening tab, said gripping member having a distal end portion which is substantially free and a base portion which is operably attached to the user surface of said fastener substrate, said gripping member configured to intersect said fastener substrate at said base portion at an intersect location which is spaced from said construction-bond portion, is positioned to extend between said fastener substrate side edge sections, and is positioned between said construction-bond portion and said user-bond end edge section of the fastener substrate, said intersect location positioned laterally inboard from a terminal, free edge of said user-bond end section of said fastener substrate by a spacing distance.

15. An article as recited in claim 14, wherein said fastening tab securing means has a leading region positioned toward said user-bond end edge section and a trailing region positioned toward said construction-bond portion of said fastener substrate; and wherein said gripping member is configured to intersect said fastener substrate at a location which is intermediate said leading region and trailing region of said securing means.

16. An article as recited in claim 14, wherein said fastening tab securing means includes means for providing an adhesive securement.

17. An article as recited in claim 14, wherein said fastening tab securing means includes means for providing a cohesive securement.

18. An article as recited in claim 14, wherein said fastening tab securing means includes means for providing an interengaging mechanical securement.

19. An article as recited in claim 18, wherein said fastening tab securing means comprises a hook component of a hook-and-loop fastener.

20. An article as recited in claim 18, wherein said fastening tab securing means comprises a loop component of a hook-and-loop fastener.

21. An article as recited in claim 14, wherein said fastening tab gripping member is positionable into a substantially parallel, adjacent relation with the user surface of said fastener substrate; and wherein said distal end portion of said gripping member extends beyond said user-bond end edge section when said gripping member is positioned into said substantially parallel, adjacent relation.

22. An article as recited in claim 14, wherein said fastening tab gripping member has a sheet configuration which intersects said fastener substrate at said base portion of the gripping member and along a line which extends approximately along a longitudinal-direction of said fastener substrate.

23. An article as recited in claim 14, wherein said fastening tab gripping member has a strip configuration which intersects said fastener substrate at a location which is intermediate said side edge regions of said fastener substrate.

24. An article as recited in claim 15, wherein said leading region of said securing means is spatially separated from said trailing region of said securing means by a selected distance which is substantially non-securing.

25. An article as recited in claim 14 wherein said leading region of said securing means is substantially coterminous with a laterally terminal edge of said fastener substrate.

26. An article as recited in claim 14, further comprising:
a backsheet layer;
a topsheet layer connected to said backsheet layer; and
an absorbent body sandwiched between said backsheet and topsheet layers.

27. An article as recited in claim 1, wherein said gripping member is provided by a substantially L-shape component having a base and a stem; said base configured to provide said use-bond end section of said fastener substrate; and said stem configured to provide said gripping member.

28. A fastening tab as recited in claim 8, wherein said gripping member is positionable into a substantially parallel, adjacent relation with the user surface of said fastener substrate; and wherein said distal end portion of said gripping member extends beyond said user-bond end edge section when said gripping member is positioned into said substantially parallel, adjacent relation.

29. An article as recited in claim 8, wherein said gripping member is offset from a laterally terminal edge of said fastener substrate by a distance.

30. A fastening tab as recited in claim 10, wherein said gripping member has a string configuration which intersects said fastener substrate at a location which is intermediate said side edge regions of said fastener substrate.

31. An article as recited in claim 23, wherein said fastening tab gripping member has a string configuration which intersects said fastener substrate at a location which is intermediate said side edge regions of said fastener substrate.

32. An article, comprising;
a fastener section and a landing attachment section, said fastener section appointed for selectively joining to said landing attachment section; and
at least one fastening tab for joining said fastener section to said landing attachment section, said fastening tab including;
a fastener substrate having a construction-bond portion for attaching said fastener substrate to said article, a user-bond portion connected to said construction-bond portion, a user-bond end edge section, a construction-bond end edge section, a pair of opposed side edge sections, a fastening surface and a user surface;
securing means connected to said fastening surface of said fastener substrate at least along said user-bond portion thereof for joining to said landing attachment section; and
a gripping member affixed to said user surface at said user-bond portion of said fastener substrate for applying a force for removing said joining of said user-bond portion of said fastening tab, said gripping member having a distal end portion which is substantially free and a base portion which is operably connected to the user surface of said fastener substrate, said gripping member configured to intersect said fastener substrate at an intersect location which is spaced from said construction-bond portion, is positioned to extend between said fastener substrate side edge sections, and is positioned between said construction-bond portion and said user-bond end edge section of said fastener substrate, said gripping member having a sheet configuration which intersects said fastener substrate along a line which extends laterally approximately along a cross-direction of said fastener substrate.

33. An article as recited in claim 32, wherein said gripping member is offset from a laterally terminal edge of said fastener substrate by a distance.

\* \* \* \* \*